(12) United States Patent
Schicht

(10) Patent No.: US 10,591,439 B2
(45) Date of Patent: Mar. 17, 2020

(54) GEL ELECTROPHORESIS SYSTEM FOR SINGLE CELL GEL ELECTROPHORESIS

(71) Applicant: 4D Lifetec AG, Cham (CH)

(72) Inventor: Oliver Schicht, Baar (CH)

(73) Assignee: 4D LIFETEC AG, Cham (CH)

( * ) Notice: Subject to any disclaimer, the term of this patent is extended or adjusted under 35 U.S.C. 154(b) by 152 days.

(21) Appl. No.: 15/554,582

(22) PCT Filed: Mar. 7, 2016

(86) PCT No.: PCT/CH2016/000043
§ 371 (c)(1),
(2) Date: Aug. 30, 2017

(87) PCT Pub. No.: WO2016/141495
PCT Pub. Date: Sep. 15, 2016

(65) Prior Publication Data
US 2018/0095055 A1    Apr. 5, 2018

(30) Foreign Application Priority Data

Mar. 6, 2015 (CH) ........................................ 313/15

(51) Int. Cl.
  *G01N 27/447* (2006.01)
  *B01L 9/00* (2006.01)
(52) U.S. Cl.
  CPC .......... *G01N 27/44782* (2013.01); *B01L 9/54* (2013.01); *G01N 27/44704* (2013.01);
  (Continued)

(58) Field of Classification Search
  CPC ........................................ G01N 27/447–44795; B01D 57/00–02; C02F 1/4696; B81B 1/00–008
  (Continued)

(56) References Cited

U.S. PATENT DOCUMENTS 4,775,003 A * 10/1988 Koh .......................... B01L 7/00
                                                   165/104.31
5,158,661 A    10/1992 Hansen
(Continued)

FOREIGN PATENT DOCUMENTS

CN      1737564    2/2006
CN    202720211    2/2013
(Continued)

OTHER PUBLICATIONS

English translation of International Preliminary Report on Patentability dated Sep. 12, 2017 (Sep. 12, 2017), Application No. PCT/CH2016/000043, 15 pages.
(Continued)

*Primary Examiner* — Bach T Dinh
(74) *Attorney, Agent, or Firm* — Rankin, Hill & Clark LLP

(57) ABSTRACT

A gel electrophoresis apparatus for single cell gel electrophoresis, including a chamber for receiving a gel electrophoresis buffer, a functional cover for closing the chamber, at least one pair of electrodes for generating a homogeneous electric field in the chamber and at least one retaining element for receiving and positioning at least one support plate. The at least one retaining element positions the at least one support plate in the homogeneous electric field generated by the at least one pair of electrodes.

18 Claims, 17 Drawing Sheets

(52) U.S. Cl.
CPC ......... *G01N 27/44708* (2013.01); *B01L 9/56* (2019.08); *B01L 2300/0829* (2013.01)

(58) Field of Classification Search
USPC ............... 204/450–470, 546–550, 600–621, 204/643–645
See application file for complete search history.

(56) References Cited

U.S. PATENT DOCUMENTS

| | | | |
|---|---|---|---|
| 5,259,943 A | | 11/1993 | Kozulic et al. |
| 2011/0024293 A1* | | 2/2011 | Mezdour .......... G01N 27/44713 204/456 |
| 2013/0105320 A1* | | 5/2013 | Samson ........... G01N 27/44756 204/461 |

FOREIGN PATENT DOCUMENTS

| | | |
|---|---|---|
| DE | 10 2007 046 615 | 4/2009 |
| EP | 1 887 349 | 2/2008 |
| EP | 2 484 749 | 8/2012 |
| EP | 2 587 257 | 5/2013 |
| WO | 2009/039822 | 4/2009 |
| WO | 2009/127911 | 10/2009 |
| WO | 2009/134768 | 11/2009 |
| WO | 2015/079048 | 6/2015 |

OTHER PUBLICATIONS

English translation of Chinese Search Report dated Apr. 23, 2019, Application No. 201680013900.7, 2 pages.

* cited by examiner

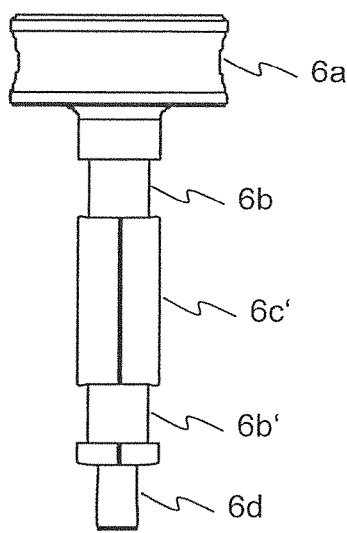
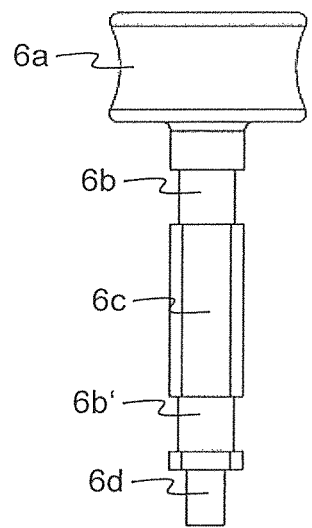
Fig. 2a     Fig. 2b
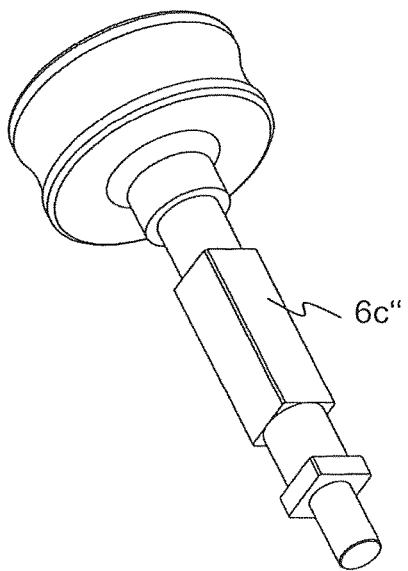
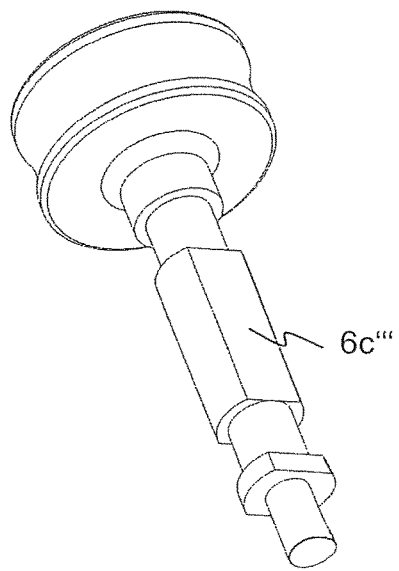
Fig. 2c     Fig. 2d

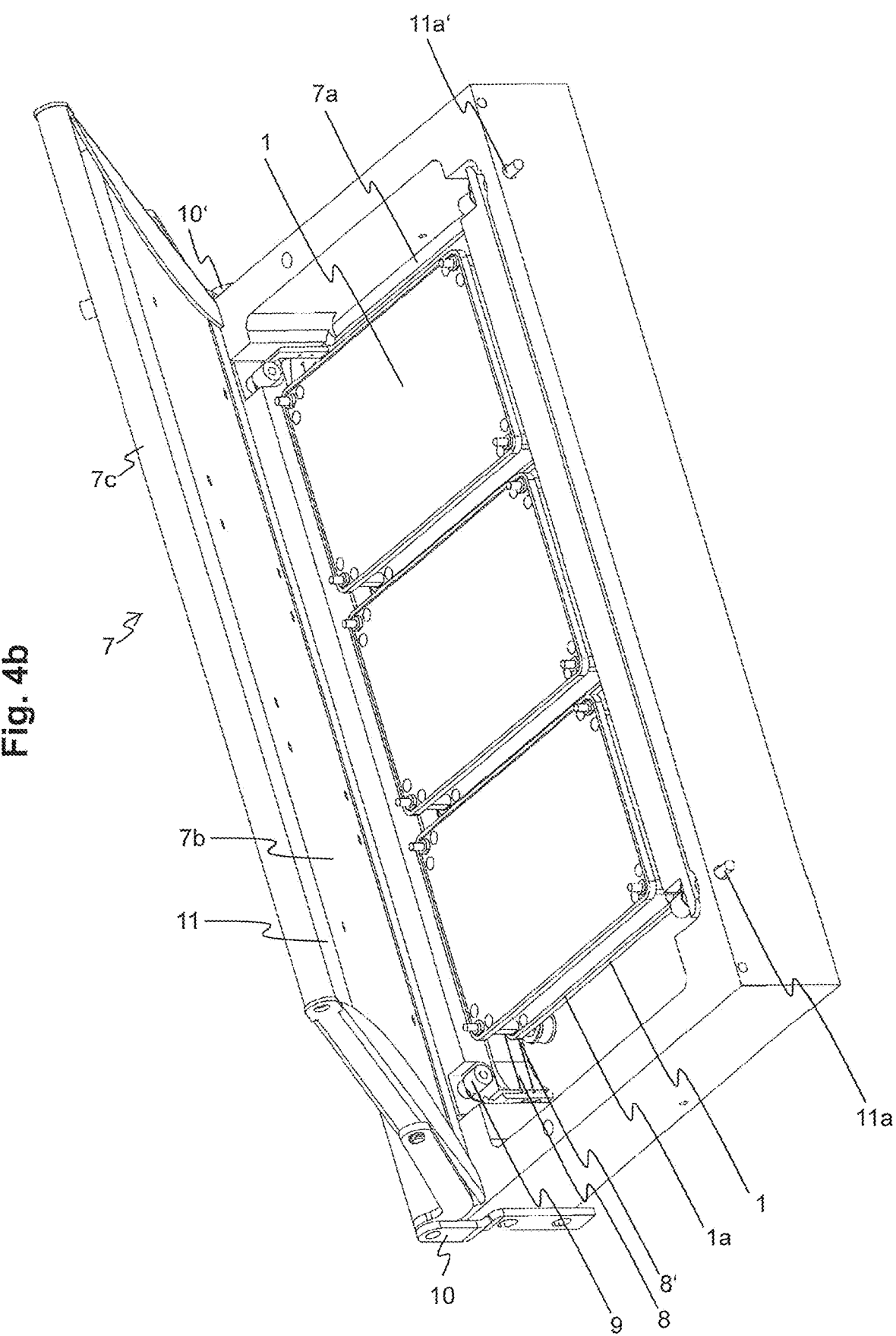

GEL ELECTROPHORESIS SYSTEM FOR SINGLE CELL GEL ELECTROPHORESIS

BACKGROUND OF THE INVENTION

Field of the Invention

The invention relates to the field of chemical and molecular-biological analysis. More particularly, the invention relates to a gel electrophoresis device, a carrier plate for receiving at least one gel, a handling frame for the carrier plate, a pipetting aid, a gel electrophoresis system and software for the control of a gel electrophoresis system.

The present invention moreover encompasses a method for the analysis of nucleic acids generally and in particular a method for carrying out a single cell gel electrophoresis (comet assay).

Description of Related Art

Single cell gel electrophoresis, also called comet assay, is a sensitive method for the direct detection of DNA single-strand breaks and double-strand breaks, which can arise due to different causes, such as, for example, due to the influence of environmental toxins, due to chemical reactions as a result of taking medicine, or generally due to chemical reagents that react with DNA. Physical influences such as ionising radiation either alone or in interaction with chemical reagents can cause damage to DNA.

The effects of environmental toxins, chemical reagents, medicine or radiation upon an organism are often proven by way of extensive animal trials, which cannot always be ethically justified and the validity of which is often disputed. Single cell gel electrophoresis has been ascertained as being a tried and tested method, in order to identify, for example, mutagenic and carcinogenic environmental toxins or to screen new active ingredients, such as, e.g., cytostatic drugs. The application of single-cell gel electrophoresis has helped to reduce animal trials in industry, research and in the clinical field.

Single cell gel electrophoreses for determining gene toxicity of already known and newly developed active ingredients are of increasing importance, particularly for the pharmaceutical industry and are increasing applied there on a large scale. In turn, this demands systems that are efficient, permit a high throughput of samples and at the same time provide reproducible results.

Individual cells, which were previously extracted from blood or tissue samples, are subjected to a gel electrophoresis with the help of single cell gel electrophoresis or the comet assay for detecting DNA damage. These cell samples are either taken from individuals who were exposed, for example, to an environmental toxin, or healthy cells are exposed to the respective substances for the evaluation of potential active ingredients and toxins. The cells to be examined or treated are embedded, e.g., into agarose and are deposited as so-called gel spots onto a carrier material such as, for example, onto an object carrier or film, lysed and either treated in an alkaline manner in order to denature the DNA or, however, kept in a neutral environment. The subsequent electrophoresis leads to the fragmented DNA removing itself from the cell nucleus due to the formation of an electrical field, i.e. the negatively charged DNA fragments travel to the plus pole and here produce a co-called "comet". The quantity of DNA which has drifted out of the head of the comet into the tail is quantified and serves as a measure of the DNA damage present in the sample. The quantification is mostly effected by way of fluorescence microscopy and is effected in a manual, partly automated or fully automated manner.

Conventional gel electrophoresis devices consist of a buffer chamber, which receives the carrier material with the gel spots located thereon, on an elevated rest surface (horizontal plate). The electrophoresis is often carried out in cold spaces or in a manner cooled by an external cooling system, in order to ensure an approximately constant temperature and to prevent an overheating of the gel spots.

The conventional gel electrophoresis systems for comet assays provide acceptable results, however, again and again it has been found that the results can vary greatly from laboratory to laboratory, from user to user in the same laboratory and even from gel to gel and assay to assay, and for example the same sample in an independent examination in 12 different laboratories can result in a DNA damage of 20% up to 80%, which corresponds to a factor of four. The causes for such a low reproducibility are to be found in the preparation of the gel spots (samples) as well as the non-standardised electrophoresis conditions for the gels, such as, for example, fluctuations in the temperature of the buffer solution during the electrophoresis, in the distance between the electrodes and/or in the buffer height and in the content of ions of the buffer above the gel spots. The basic construction of today's electrophoresis systems leads to non-specific electrical fields and inhomogeneous running conditions and therefore to a different separation of equal cell samples or DNA samples from assay to assay and thus to non-reproducible results.

Approaches for solving these problems are described in the state of the art. For example, cooling elements, which are attached below the gel platform and are connected to an external water supply, are used for approximately maintaining the temperature. However, a constant temperature in the electrophoresis system during an electrophoresis cannot be produced by these cooling elements. The buffer height is kept constant during the course by way of a covering of the gels (Trevigen Standardised Comet Assay System). Other currently known systems ensure a through-mixing of the highly basic (alkaline) running buffer by way of an integrated pump (U.S. Pat. No. 5,259,943, Kozulic et al.).

A further problem of conventional single cell gel electrophoresis methods is their low sample throughput. The horizontal rest surface for the carrier material in the electrophoresis chamber of the electrophoresis devices of the state of the art and which is limited in its size greatly restricts the sample throughput. If several carriers with gel spots located thereon are simultaneously processed, then the electrical field varies between the outer carriers and the inner carriers. The cells in the gel spots and which are to be examined are therefore not subjected to the same conditions and the results are only comparable to one another to a limited extent.

With a conventional assay, an object carrier of glass with one or more wells or without wells, into which wells the cells suspended in agarose are pipetted, is used for the electrophoresis. In other methods, flexible films are used, onto which films the agarose drops (gel spots), which contain the cells, are deposited by way of a multi-channel pipette. The film is stretched out on a plastic frame by way of it being hooked into four rods of stainless steel, which are located on the plastic frame, in order to prevent a slippage or folding of the film (Gutzkow et al., Mutagenesis, 1-8, 2013). Other methods apply carrier plates of glass, whose surface is roughened, in order to prevent a detachment of the gel spots (DE 10 2007 046 615). The previously described carrier materials for the gel spots have the disadvantage that they are very unstable, for example, in the case of the applied film and very easily break in the case of a firm carrier plate of glass. Moreover, an adhesion of the gel spots on a glass carrier is not always guaranteed. Even if the glass plate were to be coated with an agarose layer, an adhesion is still not guaranteed by way of this. Valuable samples are lost on account of this. Both materials therefore represent a certain risk during the further working procedures after the deposition of the gel spots that contain the cells. The carrier plate with the gel spots or the film is brought into a lysis buffer, then subjected to electrophoresis, brought into a fluorescing staining solution, rinsed and finally subjected to an automated microscopic analysis. This extensive handling or treatment demands an excellent adhesion of the gel spots on the carrier material, a certain stability and breakage resistance as well as resistance of the carrier plate or film to different solvents and buffers that are to be applied during the method.

The distances of the gel spots can also be variable depending on the deposition manner. It is very important for the centres of the gel spots to always be positioned in the same manner and therefore for the evaluation of the gel spots to be based on standardised conditions, for an automated microscopic evaluation of the electrophoresis results. The state of the art, for example, describes the use of a master plate with 12 or 96 openings for a more precise positioning of gel spots on the carrier material. The master plate is positioned above the carrier plate but is not fixed, which can easily lead to a slipping during the deposition of the gel spot and, therefore, to gels spots on the carrier material which are not uniformly distanced.

The examples of the state of the art, which have been mentioned above, clearly demonstrate the fact that there exists the urgent necessity for standardised conditions on carrying out single cell gel electrophoresis or comet assays.

SUMMARY OF THE INVENTION

It is therefore the object of the present invention to provide a suitable gel electrophoresis device, a gel electrophoresis system, a carrier plate for receiving at least one gel, a handling frame for the carrier plate, a pipetting aid, software for the control of a gel electrophoresis system as well as a method for carrying out single cell gel electrophoreses or comet assays, which ensure a high reproducibility of the achieved results with a simultaneous high efficiency of the sample throughput and apart from a high reproducibility permits a high sample throughput. Here, the system can be highly sensitive and specific and be simple, quick and efficient in its handling.

A further object of the present invention is to provide appliances for the optimised deposition of gel spots and their subsequent handling.

A first embodiment of the invention comprises a gel electrophoresis device for single cell gel electrophoreses with a high reproducibility, wherein the gel electrophoresis device comprises
- a chamber for receiving a gel electrophoresis buffer,
- a functional lid (cover) for closing the chamber,
- at least one electrode pair for producing a homogeneous, electrical field in the chamber, and
- at least one retaining element for receiving and positioning at least one carrier plate.

The at least one retaining element is configured to position the at least one carrier plate in the homogeneous electrical field, which is produced by the at least one electrode pair.

A precise positioning of the carrier plate in the homogeneous electrical field is rendered possible by way of this, by which means the high reproducibility of the gel electrophoresis, in particular of the single cell gel electrophoresis is rendered possible. In other words: the high reproducibility of the single cell gel electrophoresis is rendered possible with the help of the retaining elements by way of the precise positioning of the carrier plate in the chamber relative to the produced field.

An embodiment of the present invention encompasses an improved carrier plate for gel spots. The carrier plate for receiving at least one gel or gel spot includes a planar surface. A polyester film with a hydrophilic surface can be deposited on the planar surface, which means that at least the side of the polyester film, which faces away from the carrier surface, has hydrophilic characteristics.

A further embodiment includes a carrier plate with a planar surface, wherein the planar surface is treated with a hydrophilic layer.

The planar surface of the carrier plate, which has the polyester film and/or the hydrophilic layer, can also be called the hydrophilic side.

The carrier plate can be foursquare, in particular rectangular.

The carrier plate can include an edge region with at least one, in particular two, in particular three, in particular four openings, for receiving and positioning on at least one retaining element. The edge region of the carrier plate extends in the region of the edges of the carrier plate.

Such an opening can be arranged at the corners. The opening can be round, oval or polygonal or have every other conceivable shape. The opening can also be designed in a keyhole-shaped manner. A keyhole-shaped opening includes a first region and a second region, wherein the first region has a larger diameter than the second region and the first region is adjacent to the second region. In other words: the first region is essentially circular and the second region is designed as an indentation that connects to the first region.

In an embodiment, the carrier plate can include an edge region with 2 to 4 openings, wherein with regard to the shaping, at least one of the openings or its surrounding area differs from the other openings or their surrounding area. It can be the case that the openings and/or their surrounding is conformant with a shape of a fastening element, e.g. of the retaining element, for the carrier plate in a gel electrophoresis device. By way of the different shaping, it can be ensured that the carrier plates with the deposited gel spots are always brought into the gel electrophoresis device in the same orientation.

In another embodiment, the carrier plate can include a first opening in a first edge region along a first transverse side of the carrier plate and can include two further openings in a second edge region along the opposite second transverse side of the carrier plate. Given a corresponding complementary arrangement of retaining elements, an orientation specific positioning of the carrier plate on the functional lid or in the chamber is rendered possible on account of this asymmetrical arrangement of the openings in the edge region of the carrier plate. By way of the asymmetrical arrangement of openings in the carrier plates and retaining elements of the gel electrophoresis device, it can be ensured that the carrier plates with the deposited gel spots are always introduced into the gel electrophoresis device in the same orientation.

In a further embodiment, the carrier plate can include at least two first openings in a first edge region and can include at least two further second openings in the opposite second edge region. Here, the first openings are arranged asymmetrically to one another with respect to their distribution along the respective transverse side of the carrier plate. The carrier plates with the deposited gel spots can always be brought into the gel electrophoresis device in the same orientation in this manner.

Of course, the openings can also be arranged along the longitudinal side of the carrier plate, as described. It is also possible for the openings to be arranged asymmetrically in the edge region of the transverse side and/or longitudinal side.

The carrier plates of the present invention, with regard to their dimensions correspond for example to the ANSI standards (American National Standards Institute) for plates with 12 to 96 wells (ANSUSLAS 1-2004, ANSUSLAS 2-2004, ANSUSLAS 3-2004, ANSUSLAS 4-200, ANSUSLAS 6).

In a further embodiment, the carrier plate includes a transparent flexible film of polyester which includes a treated hydrophilic side and an untreated hydrophobic side. Films of this type, as such, are known in the state of the art (Lonza, GelBond® Film). In one embodiment of the invention, the film with its untreated hydrophobic side is fixed, for example, by way of bonding on the carrier plate.

In a further embodiment of the present invention, the carrier plate includes no film, but is itself treated with a hydrophilic layer for an improved adhesion of the gel spots. Here, it can be the case that the parts of the planar surface, one or more sides, or the complete carrier plate is treated with a hydrophilic layer.

In a further embodiment, the surface of the carrier plate, onto which surface a film is deposited is characterised by its planarity, which permits a uniform formation of the gel spots that are to be deposited thereon. Furthermore, the planarity of the carrier plate surface is of a huge significance for the microscoping procedure with the evaluation of the results, which is subsequent to the gel electrophoresis, since the microscope does not need to be constantly refocused, by which means the procedure of evaluation is significantly accelerated.

In a further embodiment, the film is bonded to a side of the carrier plate, which includes a planar surface, by which means a folding is prevented and the planarity of the film is ensured. Moreover, a slippage of the film on handling the carrier plate is avoided. Alternatively, the film can be spanned out onto the carrier plate, wherein the edge region of the carrier plate is designed as a frame, into which the film can be tensioned/clamped.

In an embodiment of the carrier plate, the surface, which includes the film can be recessed in a manner such that the film, which is bonded-on and/or spanned out in the recess, and the edge of the carrier plate are located at one height, i.e., form a plane. This has the advantage that the gel spots, which are to be deposited onto the film, are at the same height as the carrier plate edge, which simplifies the microscopy procedure.

In an embodiment, the side of the film that is facing away from the carrier plate, the so-called upper side of the film, which corresponds to the hydrophilic side, is pre-treated in a manner such the gel spots, which are deposited on this, adhere on the surface. The gel spots with the samples (DNA), which are to be examined and which are enclosed therein, can thereby be covalently bonded onto the treated hydrophilic side of the film, by which means a detachment and displacement of the gel spots or their shifting above one another can be prevented during the electrophoresis procedure and/or subsequent further treatment steps such as washing, staining and/or subsequent microscopic evaluation. Almost no loss of gel spots arises during the complete handling on account of this, by which means apart from the reproducibility, the efficiency of the complete method is also significantly increased compared to the methods of the state of the art.

Gel electrophoreses can be carried out in the neutral range as well as in the highly basic (alkaline) range. With single cell gel electrophoreses in an alkaline environment, the electrophoresis buffer can have a pH-value of more than 13, preferably pH 14. It is therefore advantageous if the carrier plate meets the high demands with regard to resistance to solvents in the highly alkaline range, thus includes an alkali-resistant material, for example is coated with an alkali-resistant material.

The carrier plate can consist of a transparent, organoplastic material such as for example polystyrene, polypropylene and polyterephthalate.

In a further embodiment, the plate is breakage-resistant and torsion-resistant, in order for example to endure a handling by way of a robot gripping arm, which in an automated method moves the carrier plates between the gel electrophoresis chamber and/or the staining chamber and/or de-staining chamber and/or the microscope. The material of the carrier plate can have a breakage resistance of at least 15 to 20 Newton, preferably of 16 to 18 Newton.

Concerning a further embodiment of the invention, the carrier plate not only serves as a carrier for the sample to be examined, but also functions as a washing and/or staining appliance for the gel spots that contain the samples. For this, an outer frame can be deposited onto the carrier plate. The washing solutions and/or staining solutions can be applied directly onto the carrier plate. For example, highly mutagenic ethidium bromine can be used as a staining solution. Contact with such a mutagenic compound should be avoided. As already described, the washing and/or staining solution can be deposited directly onto the carrier plate with the help of the outer frame and a draining of the washing solution and/or staining solution away from the carrier plate can be prevented by the outer frame, wherein the outer frame, which is elevated with respect to the carrier plate, acts as a dyke or dam. The awkward handling of the carrier plates when these are brought into the various containers provided for the washing procedures and/or staining procedures is therefore omitted on account of this. Moreover, the carrier plate is not contaminated as a whole, for example with the mutagenic staining solution, but only in the region of the samples or the gel spots.

The opening of the carrier plate can be designed as a blind hole and/or as a continuous recess, thus extend through the complete thickness of the carrier plate.

The carrier plate can include a spacer element in the edge region, on the side of the carrier plate that is away from the hydrophilic side. The spacer element can be arranged in the surrounding of the opening, wherein the spacer element can surround the opening in a hollow-cylinder-shaped manner. The hollow-cylinder-shaped spacer element can include at least one slot that extends from one base surface in the direction of the other base surface of the hollow cylinder. The spacer element obtains elastic or resilient characteristics in the manner, and these simplify the introduction or positioning with a retaining element. The spacer element can also be designed in a pin-shaped or pin-like manner with a round or polygonal or arbitrarily shaped cross section. The spacer element can also be arranged independently of the position of the opening in the edge region. The carrier plate can include at least two, in particular at least three, in particular at least four spacer elements in the edge region. In particular, the spacer elements can be arranged on opposite transverse and/or longitudinal sides of the carrier plate. By way of this, it is possible for several carrier plates to be able to be stacked above one another, without affecting the gel spots/samples that are located thereon, by which means a storage of the carrier plates with the samples deposited thereon, for example in a fridge, can be simplified. The spacer element can also permit a simple positioning of the carrier plate in the electrophoresis tank.

A further embodiment relates to a handling frame for the carrier plate. The handling frame, for example at the corners and/or on its longitudinal or transverse sides, includes at least one fastening means for receiving a carrier plate. The fastening means can include a base part and a pin-like prominence. It can be the case that the base part is seated on the handling frame and the pin-like prominence for its part is seated on the side of the base part, which is away from the handling frame. The fastening means, in particular a base part and a pin-like prominence can be designed such that it positively fits into an opening of the carrier plate and/or matches a surrounding of an opening on the carrier plate. The prominence can be designed in a pin-like manner. The base part can be round, polygonal, oval or be designed in another arbitrary shape.

The handling frame permits an insertion and removal of the carrier plate into and out of the highly alkaline electrophoresis buffer of the gel electrophoresis chamber as well a transfer into washing and/or staining solutions, the insertion, removal and transfer being accomplished without the user becoming contaminated. Such a handling frame can also be applied, for example, in gel electrophoresis systems of the state of the art.

A further embodiment relates to a pipetting aid for single-channel or multi-channel pipettes, including a pipetting block and a frame. The pipetting aid can be of a transparent organoplastic material.

The pipetting aid can include conical passages, which means that the diameter of the passages can become narrower in one direction. For example, it can be the case that a lower outlet has a smaller diameter than an upper inlet. In another embodiment, the passages can be designed cylindrically, i.e. the diameter of the passages remains constant, which means that the inlet and outlet openings have the same diameter.

The pipetting aid can have up to 96 passages.

The pipetting aid includes a frame, for example of plastic or metal, in particular of stainless steel.

The frame can be fixedly connectable to the pipetting block, for example at the longitudinal side.

It can be the case that the frame projects beyond the pipetting block at one side, for example at the side of the lower outlets.

The frame can include a recess having the size of the carrier plate. For the pipetting procedure, the frame with the recess is placed onto the carrier plate, by which means the carrier plate is received in the frame of the pipetting aid in an exactly fitting manner and cannot slip during the pipetting procedure. This means that the carrier plate is positionable into the recess of the frame in an exactly fitting manner. In particular, it can be the case that the recess of the frame is designed for carrier plates according to the ANSI standards mentioned above. This permits the pipetting of uniformly shaped and equally large gel spots onto the carrier plate or onto the film which is located on the carrier plate, at regular distances and ensures that the centre of the spots is located in a defined region and can be found and put under the microscope rapidly and without any problem given an automated microscopic evaluation.

A gel electrophoresis system can include a gel electrophoresis device as well as further components.

The gel electrophoresis system can include:
an integrated means for the temperature control and/or
an integrated means for cooling and/or heat production,
in particular for maintaining a constant temperature in the gel electrophoresis device during the gel electrophoresis procedure.

In an embodiment, a gel electrophoresis system can include an integrated means for the buffer circulation,
in particular an integrated means for the buffer circulation, by way of which means a uniform ion distribution and temperature distribution in the buffer solution can be ensured during electrophoresis.

In an embodiment, a gel electrophoresis system can include:
an integrated voltage generating device, and/or
an integrated mains connection device, and/or
an integrative software, and/or
a subsequently arranged, integrated and automated analysis device for the quantification of the obtained results, and/or
a digital interface for the further processing of the results.

In an embodiment, data of measuring electrodes and/or data of a means for the temperature control can be acquired and optionally recorded by software, which is integrated in the gel electrophoresis device. The software can control and/or regulate a means for the voltage generation, a means for the buffer circulation and/or a means for cooling and heat production, on the basis of this data. Should the measured values deviate from a given value range, then the software controls the means specified above such that values which deviate from the set points are corrected. In this manner, it is possible to keep parameters within a certain parameter range, in particular essentially constant, during the complete electrophoresis procedure. Constant conditions, for example a constant electrical field in the region of the carrier plates with the gel spots, can be ensured by way of this.

In an embodiment, the electrophoresis chamber of the gel electrophoresis device, thus the chamber for receiving the gel electrophoresis buffer, can be closed with a functional lid. The closure mechanism is designed, for example, as a magnet. In a further embodiment, the opening of the functional lid interrupts the flow of current in the chamber. Injury to the user, for example, can be prevented by way of this.

The functional lid can include a grip/handle for the simple opening and closing of the electrophoresis chamber.

The functional lid can be connected to the electrophoresis chamber at both transverse sides by way of hinge joints, for a uniform sliding during the closing and opening procedure of the electrophoresis chamber. Such hinge joints can be arrestable (lockable). If retaining elements are arranged on the functional lid and the hinge joints are arrestable, then the carrier plates can be placed onto the retaining elements with pressure and/or released from these again, in the opened condition of the functional lid, without the lid thereby moving. It is possible for the functional lid to be designed as a folding lid and to be connected to the electrophoresis tank by a folding hinge.

The connection of the functional lid to the electrophoresis tank can include a brake. An undesired closing of the functional lid and damage to the samples, which are deposited on a carrier plate positioned on the functional lid, can be prevented by way of this. The integrity of the samples can be increased by way of this.

In a further embodiment of the present invention, the at least one carrier plate can be brought into the gel electrophoresis chamber, thus the chamber for receiving a gel electrophoresis buffer. If retaining elements are arranged in the inside of the chamber, in particular in and/or on the base of the chamber, then a carrier plate can be attached on one or more retaining elements. The carrier plate with at least one opening can be stuck and/or fixed onto at least one retaining element if the carrier plate includes corresponding openings.

In an embodiment, for example 1 to 12 retaining elements are arranged in the inside of the chamber and, for example, 1 to 6 carrier plates can be brought into the chamber. These carrier plates can be arranged, for example, in a horizontal, sandwich-like manner or vertically with intermediate spaces between the carrier plates, and the gel electrophoresis buffer can flow freely around these plates.

The functional lid can be designed in a manner such that on its side, which faces the chamber, the lid includes the at least one retaining element for receiving and positioning at least one carrier plate.

If the functional lid is opened after carrying out the gel electrophoresis, the at least one carrier plate, which is fastened on the functional lid, is lifted out of the gel electrophoresis buffer, which is located in the chamber, and the gel electrophoresis buffer can run off from the at least one carrier plate located in the functional lid. The user therefore no longer comes into contact with the gel electrophoresis buffer as is the case with conventional devices.

The retaining elements can be designed in a manner such that the at least one carrier plate with at least one opening can be stuck and fixed on the at least one retaining element.

According to an embodiment of the functional lid, said functional lid can include at least 1 to 12 retaining elements and receive, for example, 1 to 6 carrier plates. For example, three carrier plates can be fixable horizontally in a plane of the functional lid in this manner. Further carrier plates can be fixable above and/or below these horizontally arranged carrier plates in a sandwiched manner. Other arrangements, such as a vertical arrangement of the carrier plates in the functional lid are also possible, alternatively to such a horizontal arrangement.

In an embodiment, the gel electrophoresis device is configured such that the at least one carrier plate can be immersed into the gel electrophoresis buffer, which is located in the chamber, and the gel electrophoresis buffer can flow freely around this plate, after the closure of the functional lid. In a system that is configured for the simultaneous immersion of several carrier plates, an intermediate space can be located between two carrier plates in each case, so that each of the immersed carrier plates can be freely peripherally subjected to flow of the electrophoresis buffer. In other words: the at least one retaining element of the gel electrophoresis device is configured to receive the at least one carrier plate in a manner such that gel electrophoresis buffer can flow freely around the carrier plate in the chamber.

In an embodiment, at least one of the retaining elements or parts of these is/are designed as a measuring electrode for measuring an electrical field. The electrical field can be continuously measured and the measured data transferred for example to software during the electrophoresis procedure by way of this. Here, for example, the electrical field over the at least one carrier plate and/or several carrier plates and/or between two carrier plates can be measured and be controlled by the software.

In an embodiment, at least two of the retaining elements are designed as measuring electrodes.

In a further embodiment, the gel electrophoresis device can include a measuring electrode, which is designed independently of the retaining element. Such a separate measuring electrode is also configured to measure the electrical field over the at least one carrier plate and/or over several carrier plates and/or between two carrier plates. The measuring electrode can be designed as a pin.

The measuring electrode can include a measuring region, which is arranged in the chamber in a manner such that it lies on the retaining element in the positioned condition of the carrier plates and between the carrier plates in the closed condition of the gel electrophoresis device. The electrical field can be measured in the proximity of the carrier plate by way of this, and possibly controlled with the help of software. Here, the measuring electrode can be coated with an electrical insulator and only permit measurements of the electrical field in the measuring region.

Here, some of the retaining elements can differ from the remaining retaining elements with regard to the shaping. Analogously, some of the openings and/or surrounding of the openings of a carrier plate can differ in shaping from the other openings and/or surroundings of the openings of the carrier plate, and specifically such that the different retaining elements can be connected exclusively to the differing openings. An unambiguous origination of the carrier plate in the electrophoresis chamber, thus the chamber for receiving the gel electrophoresis buffer, can be defined by way of this. It is possible for all carrier plates respectively for all gels spots, which are with the samples to be examined and which are located on these carrier plates, to define the running direction of the electrophoresis by way of this.

If more than one carrier plate is simultaneously subjected to an electrophoresis, then in a preferred embodiment of the present invention, two carrier plates can each be arranged in a manner such that the gel spots attached thereto face one another (face-to-face).

The electrical field that is produced by the electrodes can be at its most homogenous between two carrier plates, around which the buffer solution can freely flow, wherein the position of the carrier plates in the electrical field is decisive for the quality of the reproducible electrophoresis. For example, the electrodes of the electrode pair can be arranged at the same height and be essentially matched to the position of the carrier plate in the closed condition of the gel electrophoresis device, wherein the position of the carrier plate is determined or defined by the retaining elements. In particular, the electrode pair can be arranged at the height of the carrier plate in the closed condition of the gel electrophoresis device.

The carrier plates can be arranged, for example, in a manner such that the gel spot side thus the hydrophilic side of the one carrier plate faces the lower side of the carrier plate carrier plate, which is arranged thereabove or therebelow (face-to-bottom). A lower side indicates the flat side of a carrier plate that lies opposite the flat side with the gel spots (also called upper side).

Moreover, the carrier plates can be arranged vertically or horizontally in a plane and/or above one another or next to one another in a sandwiched manner. In an embodiment, the arrangement is matrix-like, which means that the same amount of carrier plates can be arranged in each row and the same amount of carrier plates in each column.

In a further embodiment, the functional lid and the retaining elements are designed in a manner such that carrier plates of glass and/or object carriers are fixable in the functional lid of the gel electrophoresis chamber. Alternatively, the glass plates and/or object carriers can also be fixed in the chamber, preferably on the chamber base, by the correspondingly designed retaining elements. In other words, at least one retaining element of the gel electrophoresis device can be arranged in the functional lid and/or in the inside of the chamber, in particular in and/or on the base of the chamber.

Electrodes of acid-resistant or alkali-resistant material such as noble metals or noble metal combinations, preferably platinum-iridium can be used for producing an electrical field over the carrier plates.

In an embodiment, in each case one, preferably two electrodes which run parallel to one another are attached on opposite inner walls of the chamber in a manner such that the carrier plates, under certain circumstances with the gel spots located thereon, are located at the height of the electrodes given a closed chamber lid, thus given a closed functional lid, by which means the electrical field forms on the plane/level of the gel posts or the samples located thereon. Given an electrophoresis chamber, which is designed having a rectangular outline, the electrodes can be located on sides of the chamber that lie opposite one another. This arrangement of carrier plates and electrodes ensures a uniform electrical field over the samples to be examined.

In a further embodiment, the at least one retaining element includes a head part and at least one latch-in section for the fixation of at least one carrier plate. A carrier plate can be positioned in the electrophoresis tank by way of this.

The retaining element can be designed in an essentially pin-like manner and engage into an opening of the carrier plate, which is designed in an accordingly congruent or corresponding manner, wherein the latch-in section of the retaining element is positioned in the openings of the carrier plate in the positioned condition of the carrier plate.

The head part can be designed in a manner such that it fits through the first region of a keyhole-shaped opening of the carrier plate. The head part can be pushed through this first region of the openings. The latch-in section, which has a smaller diameter than the head part, can subsequently be positioned or latched in the second region of the keyhole-shaped opening of the carrier plate.

In another embodiment, the retaining element is designed in a rail-like manner with a groove as a latch-in section, wherein the edge region of the carrier plate can be inserted and positioned in the groove of the retaining element. The head part of the retaining element is designed as a terminating surface.

In a further embodiment, the at least one retaining element includes a first latch-in section for the fixation of a first carrier plate and a second latch-in section for the fixation of a second carrier plate, a spacer between the first latch-in section and the second latch-in section and an anchor. The anchor can be anchored in the functional lid of the electrophoresis chamber and/or can be placed or positioned in or on the base of the chamber of a gel electrophoresis device. The retaining element can be positioned relative to the chamber or to the electrophoresis tank by way of this. The spacer permits a precise positioning of two carrier plates relative to one another. The distance of two carrier plates can be matched to the position of the electrode pair or to the distance of the electrode pairs with the help of the spacer in this manner, so that both carrier plates can be arranged in the homogenous electrical field.

The first latch-in section and the second latch-in section can thereby be designed identically. It is also possible for the first latch-in section to be designed differently to the second latch-in section.

The latch-in section is designed in a manner such that the carrier plate can be fixed on the latch-in section thus is fixable or positionable, in a manner in which it can be latched in or snapped in.

The latch-in section can be designed in a pin-like or cylindrical manner and the opening of the carrier plate can be accordingly designed in a corresponding manner. It is also possible for the spacer element to be designed as a hollow-cylindrical positioning latch-in element. The positioning latch-in element can have resilient characteristics and be inserted via the head part and the latch-in section of the retaining element, and the carrier plate thus fixed on the retaining element.

The connection between the retaining element and the carrier plate can be designed in the manner of a push button, wherein the retaining element engages into the opening of the carrier plate and a precise positioning or fixation is thus rendered possible. It is also possible for the retaining element to engage into the positioning latch-in element and in this manner a relative positioning and precise fixation of the carrier plate on the retaining element is realisable. The retaining element and/or the positioning latch-in element can be designed in a slightly resilient or expandable manner, in order to permit a repeated positioning without being destroyed.

In an embodiment, the gel electrophoresis device includes a carrier element with at least one retaining element which is positionable in the electrophoresis tank, in particular in the chamber, in particular on the base of the chamber. The retaining element for this is configured to position at least one carrier plate in the homogeneous electrical field that is produced by the at least one electrode pair. The carrier element and the retaining element are dimensioned in a manner such that a carrier plate, which is fixed on the retaining element can be positioned in the produced homogeneous electrical field of the electrode pair or of the electrode pairs given a closed electrophoresis tank. By way of this, at least one carrier plate can be positioned on the functional lid with the help of the retaining element, and at least one carrier plate can be positioned in the homogeneous electrical field with the help of the retaining element, independently of one another. An increased sample throughput can be achieved by way of this. Such a carrier element can also be called a basket.

The carrier element can be placed into the chamber. The carrier element can include an incorrect-rotation safeguard. An incorrect-rotation safeguard can likewise be formed on the base of the chamber. In the manner, the carrier element can only be arranged in the chamber in a specific orientation relative to the chamber, which is to say relative to the electrophoresis tank. By way of this, it is possible for a carrier plate, which is fixed on the carrier element or on the retaining element, to be arranged in only one specific orientation relative to the produced homogeneous, electrical field of the electrode pair. In the positioned condition, the position of the carrier plate can be defined by the dimensioning of the carrier element and/or retaining element.

The carrier element can include a carrier grip/handle, which projects out of the gel electrophoresis buffer in the condition arranged in the chamber. An insertion of the carrier element into the chamber and a removal of the carrier element out of the chamber can be simplified by way of this.

The base of the chamber can have a slope that is configured such that the gel electrophoresis buffer collects at the deepest point of the descent, thus a trough, on draining or changing the gel electrophoresis buffer. In this manner, it is possible for the gel electrophoresis buffer to collect at the deepest or lowermost point of the slope or base, thus in the trough, by which means a drainage or change of the gel electrophoresis buffer is simplified.

In a further embodiment, the electrophoresis chamber, thus the chamber for receiving the gel electrophoresis buffer, or the gel electrophoresis device, includes a heat exchanger that is coupled to an internal heating and/or cooling device, which can be regulated or controlled, for example, via integrative software.

A circulation of the buffer in the chamber can be rendered possible by way of a pump that is integrated in the gel electrophoresis device. Here, at least one barrier, which has passages and which is attached vertically on the base plate, can break up the buffer flow over the carrier plates and permits a uniform flow over the at least one carrier plate. The passages of the at least one barrier can be designed in the form of a continuous, horizontal slot and/or several horizontal or vertical slots and/or horizontal tubes. Any other shape of the passages is likewise possible.

In a further embodiment, the gel electrophoresis device includes at least one barrier that is configured for producing a laminar buffer flow. In particular, the barrier can be arranged on a side of the chamber wall.

The chamber wall is a wall of the chamber for receiving the gel electrophoresis buffer.

In a further embodiment, the gel electrophoresis device includes at least one barrier having:
- at least one continuous, slot-like passage which runs horizontally, which is to say parallel to the electrodes of the chamber and/or parallel to the base of the chamber and/or parallel to the functional lid in the closed condition of the gel electrophoresis device, and/or
- several shorter, slot-like openings that run vertically, which is to say perpendicularly to the electrodes and/or perpendicularly to the functional lid in the closed condition and/or perpendicularly to the base of the chamber, and/or
- tubular passages.

A method for carrying out a single cell gel electrophoresis or a comet assay can include the following steps:
- depositing a gel spot with cells to be examined, e.g. with the help of a single-channel or multi-channel pipette, onto a carrier plate;
- positioning a carrier plate on at least one retaining element of an electrophoresis chamber;
- closing a functional lid;
- incubation of the carrier plates with the gel spots, which are deposited thereon, in alkaline environment for DNA unwinding;
- selecting a electrophoresis program and initiating a control of the electrophoresis parameters by way of integrative software, for producing a homogeneous field over the at least one carrier plate;
- opening the functional lid and removing the carrier plate;
- bringing the carrier plate into a staining solution;
- drying the gel spot in a solvent, in particular alcohol, in particular ethanol;
- removing the carrier plate from the staining tank and bringing the carrier plate into a washing solution, wherein the staining tank is a container with a staining solution;
- optionally drying the gel spot on the carrier plate;
- manual or partly-automated or automated microscopic evaluation of the gel spot.

An automated analysis for quantifying the results can also be possibly carried out.

BRIEF DESCRIPTION OF THE DRAWINGS

The subject matter of the invention is hereinafter explained in more detail by way of preferred embodiment examples, which are represented in the accompanying drawings. In each case are represented schematically in:

FIG. 2a shows a retaining element for carrier plates with a laterally flattened spacer;

FIG. 2b shows a retaining element for carrier plates as in FIG. 2a, a non-flattened side of the spacer being represented;

FIG. 2c shows a retaining element for carrier plates with a polygonal spacer;

FIG. 2d shows a retaining element for carrier plates with spacers flattened at two sides;

FIG. 4b shows a gel electrophoresis device with 3×2 carrier plates, which are located in the chamber;

DETAILED DESCRIPTION OF THE INVENTION

In principle, the same or analogous parts are provided with the same references numerals in the figures.

Figure 1A:
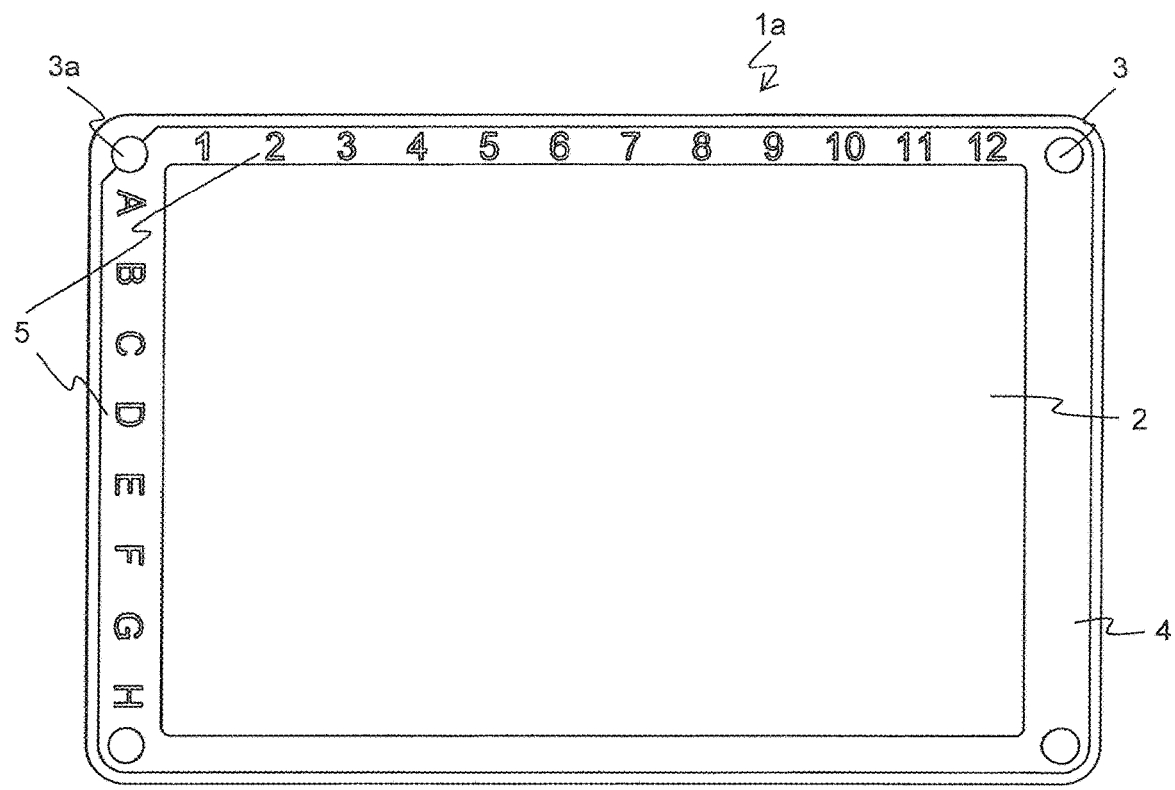
FIG. 1a is a plan view of a carrier plate with round openings at the corners.
Figure 1B:
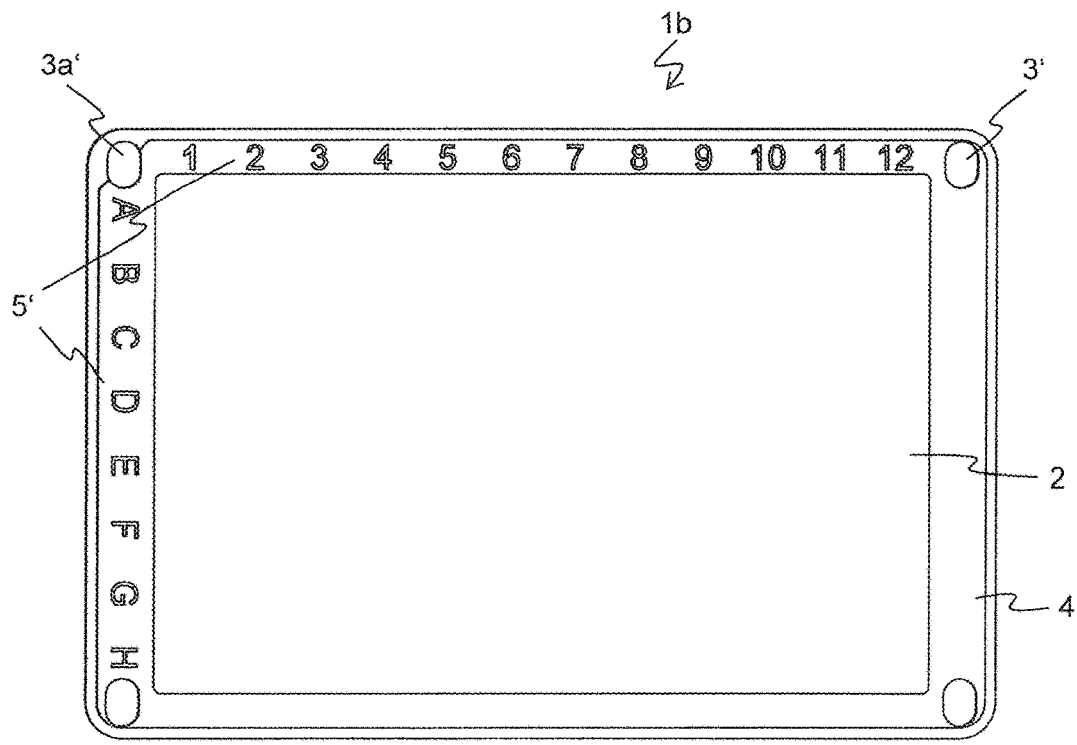
FIG. 1b is a plan view of a carrier plate with oval openings at the corners.

FIGS. 1a and 1b show a plan view of a rectangular carrier plate 1a with a film surface 2 and with an edge region 4 which is provided with markings 5 on a longitudinal and a transverse side, the markings defining a grid for the gel spots that are to be deposited onto the film. The film surface is a planar surface of the carrier plate, on which a polyester film with a hydrophilic surface is deposited. The carrier plate with the planar surface can alternatively be treated with a hydrophilic layer.

The openings 3 of the carrier plate 1a, which are at the corners, are represented in a round manner in FIG. 1a, and in FIG. 1b as oval openings. Of course, further embodiments of the openings 3, 3' such as, for example, square or rectangular openings or openings of an arbitrary shape are possible. The carrier plate 1 is bevelled in the edge region of one of the openings 3a, which is at the corner. This bevelling positively matches a retaining element, which is specially matched to this and characterises the orientation of the carrier plate 1 in the chamber 7a, which is to say determines the orientation of the carrier plate 1 in the chamber 7a.

FIG. 2a shows a retaining element for the fixation of the carrier plates 1 in an electrophoresis chamber, thus in a chamber for receiving the gel electrophoresis buffer. The retaining element 6 includes a head part 6a, a latch-in section 6b for the fixation of a first carrier plate 1, a latch-in section 6b' for the fixation of a second carrier plate, a spacer 6c', which on using two carrier plates, keeps these at a distance, and an anchor 6d, which can be anchored in the functional lid of a gel electrophoresis device or however placed or positioned in the base of the chamber of a gel electrophoresis device.

The spacer 6c' is represented in FIG. 2a with a flattened side. FIG. 2b shows the oppositely lying arched side of the spacer 6c.

FIG. 2c shows a spacer 6c'' in a polygonal embodiment with four flattened sides, and in FIG. 2d an embodiment of a spacer 6c''' with two flattened and two arched sides is represented.

The head 6a and/or the spacer 6c, 6c', 6c'', 6c''' of a retaining element 6 can be designed as a measuring electrode.

On using more than one retaining element 6, for example, one of the spacers with regard to its embodiment can differ from other spacers. Such a spacer, for example, can be adapted to an opening and/or its surrounding of a carrier plate, which differs from the other openings and/or surrounding of the carrier plate. An orientation of the at least one carrier plate 1 in the functional lid or the base of the electrophoresis chamber and which is always the same can be ensured by way of this.

Figure 3:
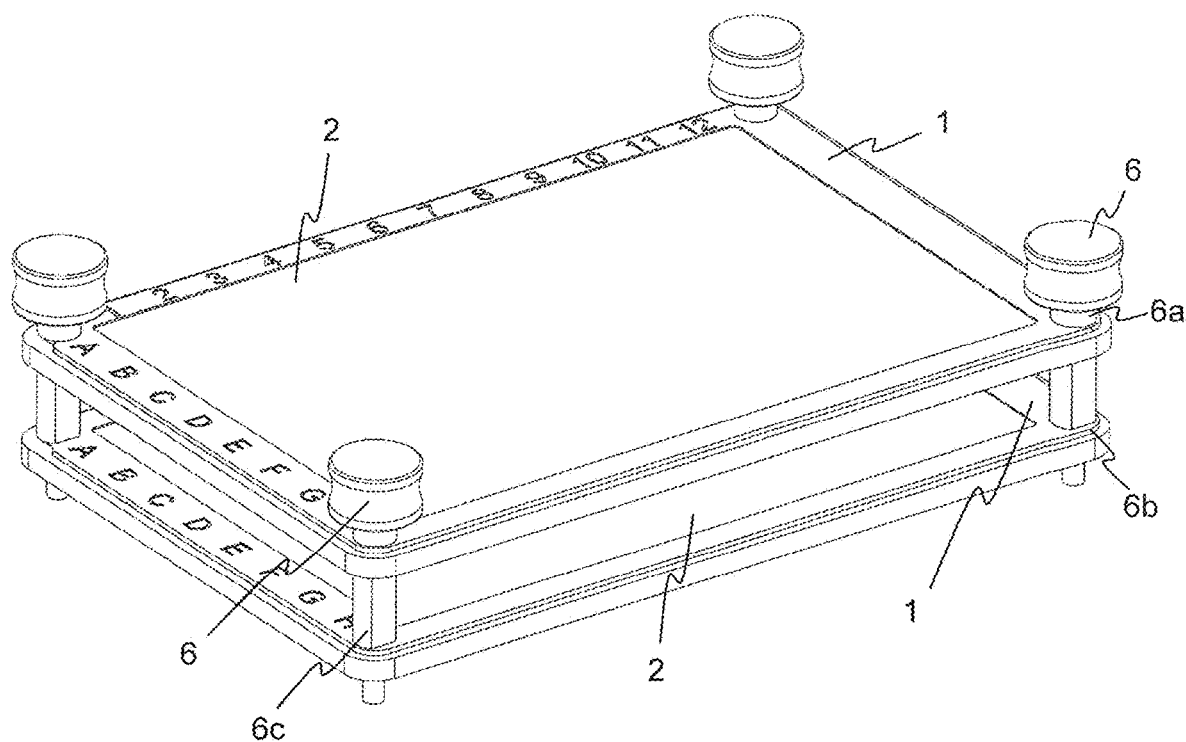
FIG. 3 shows two carrier plates, which are arranged above one another in a sandwiched manner, fixed by way of four retaining elements.

FIG. 3 shows two carrier plates 1 and four retaining elements 6 in the assembled condition. The two carrier plates 1 are assembled above one another by way of four retaining elements 6. On account of its openings, the first carrier plate 1 is fixed in the first latch-in sections 6b of the four retaining elements and the second carrier plate 1 by way of its openings is fixed in the second latch-in sections of the four retaining elements 6. Spacers 6c ensure a constant distance between the carrier plates 1. In this embodiment example, the two carrier plates are fixed in a manner such that the films 2 with the gel spots deposited thereon are arranged face-to-back. In an alternative embodiment, the carrier plates 1 are fastened in the retaining elements 6 in a manner such that the films 2 with the gel spots lie facing one another (face-to-face).

Figure 4A:
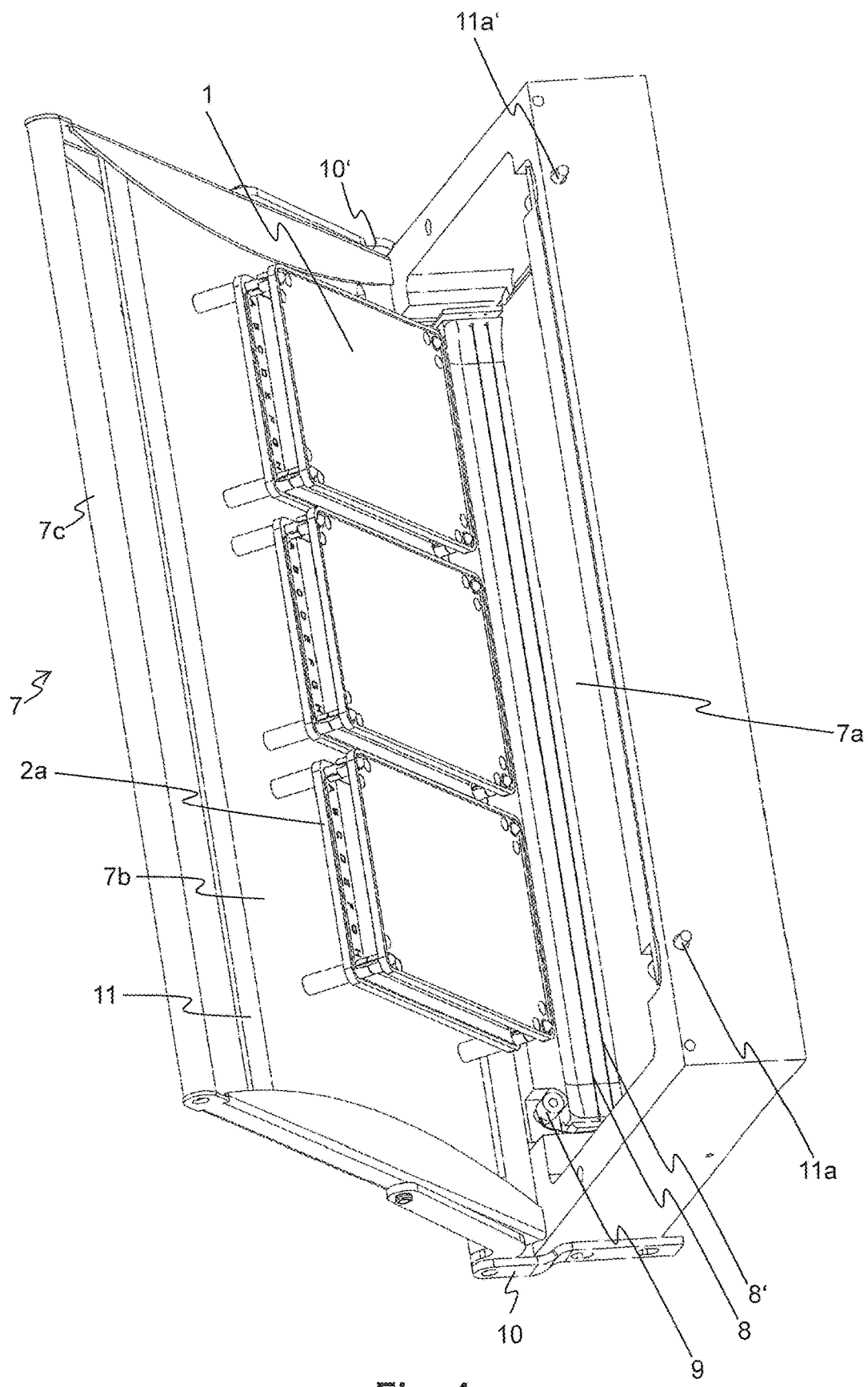
FIG. 4a shows a gel electrophoresis device with 3×2 carrier plates, which are fixed in the functional lid.

FIG. 4a shows an electrophoresis tank 7 including an electrophoresis chamber 7a, thus a chamber for receiving a gel electrophoresis buffer, a functional lid 7b and a grip 7c. The electrophoresis chamber 7a in the interior and on a longitudinal side in each case includes two electrode pairs 8 and 8', which run in parallel and which are of an alkali-resistant material such as platinum-iridium. The electrode pairs are designed as electrode wires and are fixed in the electrophoresis chamber 7a via fastening means 9. The fastening means 9 simultaneously serve as a connection between the electrode and electricity source, in particular as a conductive connection.

When the functional lid 7b is closed, then the electrode pairs 8 and 8' are located at the height of the intermediate space between the carrier plates 1 or the films, which are with the gel spots and which are located on these plates.

The functional lid 7b of the electrophoresis tank 7 on its side that is directed to the electrophoresis chamber 8a includes twelve retaining elements, which are fixed on the lid 7b. The retaining elements are arranged in three groups of four retaining elements 6. Two carrier plates are fixed face-to-face, i.e., with the film or the surface treated with the hydrophilic layer and the gels spots located thereon facing one another, per group of retaining elements. Openings for the retaining elements, into which openings the anchor of a retaining element can be introduced and fastened are incorporated or arranged in the lid of the electrophoresis chamber.

The functional lid moreover includes a grip 7c for opening and closing the electrophoresis chamber 7a. The functional lid 7b is connected to the electrophoresis chamber 7a at two transverse sides by way of hinge joints 10, 10'. These hinge joints 10, 10' can be arrestable.

Moreover, the electrophoresis tank 7 on a longitudinal side of the electrophoresis chamber 7a and on a longitudinal side of the functional lid 7b includes parts of a closure mechanism 11, 11a, 11a'. The closure mechanism can include a magnet, for example.

FIG. 4b shows an electrophoresis tank 7 including an electrophoresis chamber 7a, a functional lid 7b and a grip 7c. The electrophoresis chamber 7a in the interior and on a longitudinal side includes two electrodes 8 and 8', which run in parallel and are of an electrochemically noble material such as, for example, platinum-iridium. The electrode wires are fixed in the electrophoresis chamber 7a via fastening means 9. The fastening means 9 simultaneously serve as a connection between the electrode and electricity source.

In contrast to FIG. 4a, the carrier plates 1 shown in FIG. 4b are fastened in or on the base of the electrophoresis chamber by way of retaining elements. For this, openings, into which the anchor of the retaining elements 76 is insertable and can be fastened are incorporated in the base of the electrophoresis chamber. The retaining elements can also be in the chamber in an unfastened manner and be placed onto the base of the chamber.

Figure 5A:
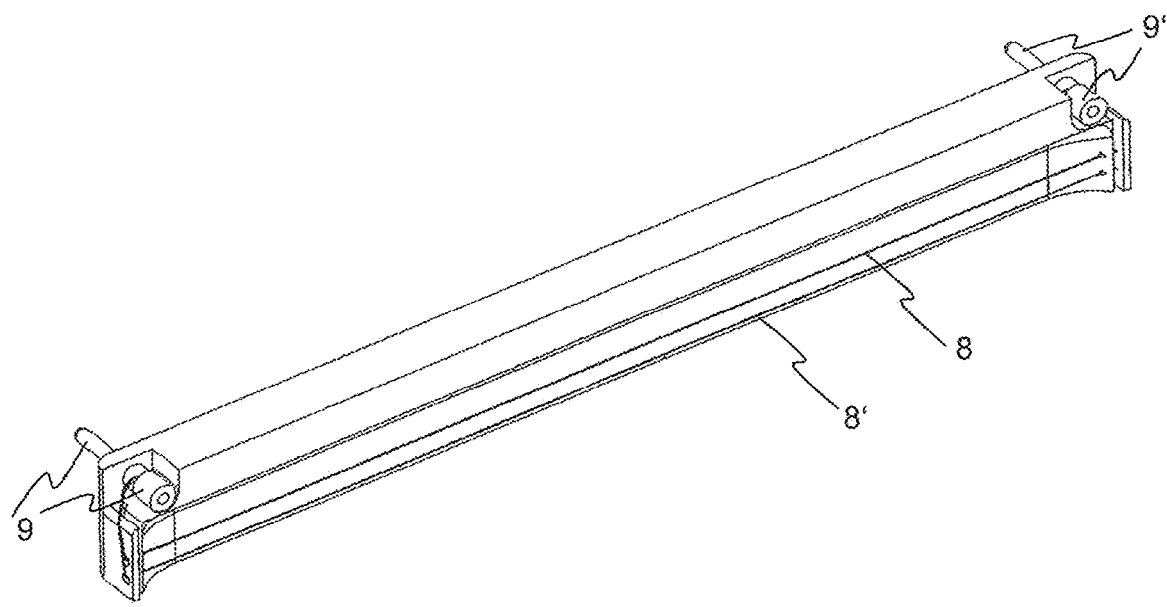
FIG. 5a and FIG. 5c show a detail of the chamber wall with fastening means for the electrodes, which are arranged in pairs.

FIG. 5a shows a detail of a longitudinal side of the electrophoresis chamber of one of the two FIG. 4a or 4b with the two electrodes of the electrode pairs 8 and 8', which run in a parallel manner on the longitudinal side and with a fastening means 9 and 9' for the electrodes 8 and 8'. FIG. 5c shows a similar detail of a longitudinal side of the electrophoresis chamber 7a. The electrode pairs 8, 8 are covered by a protective element 80 in order to prevent an unintended contact with an electrode pair 8.

Figure 5B:
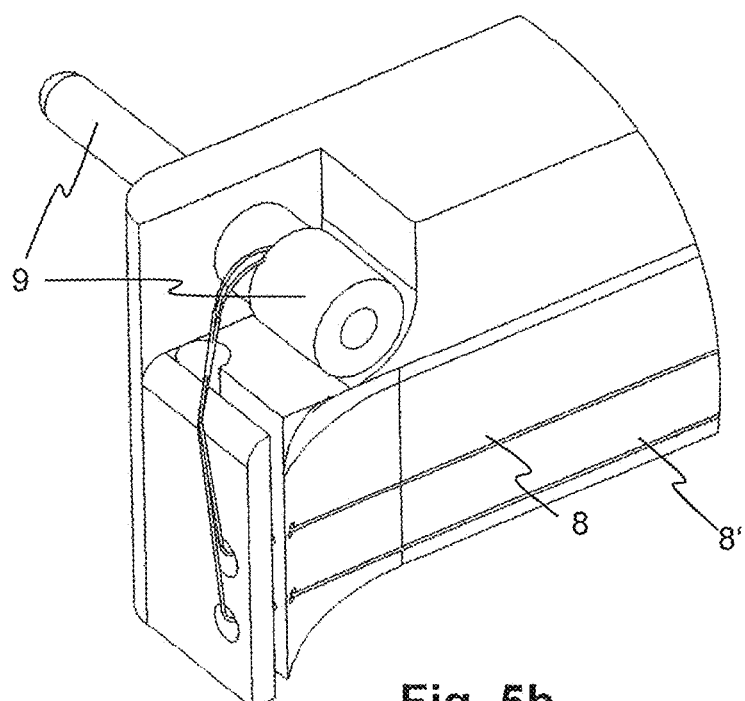
FIG. 5b shows a fastening means for electrodes, which are arranged in pairs.
Figure 5C:
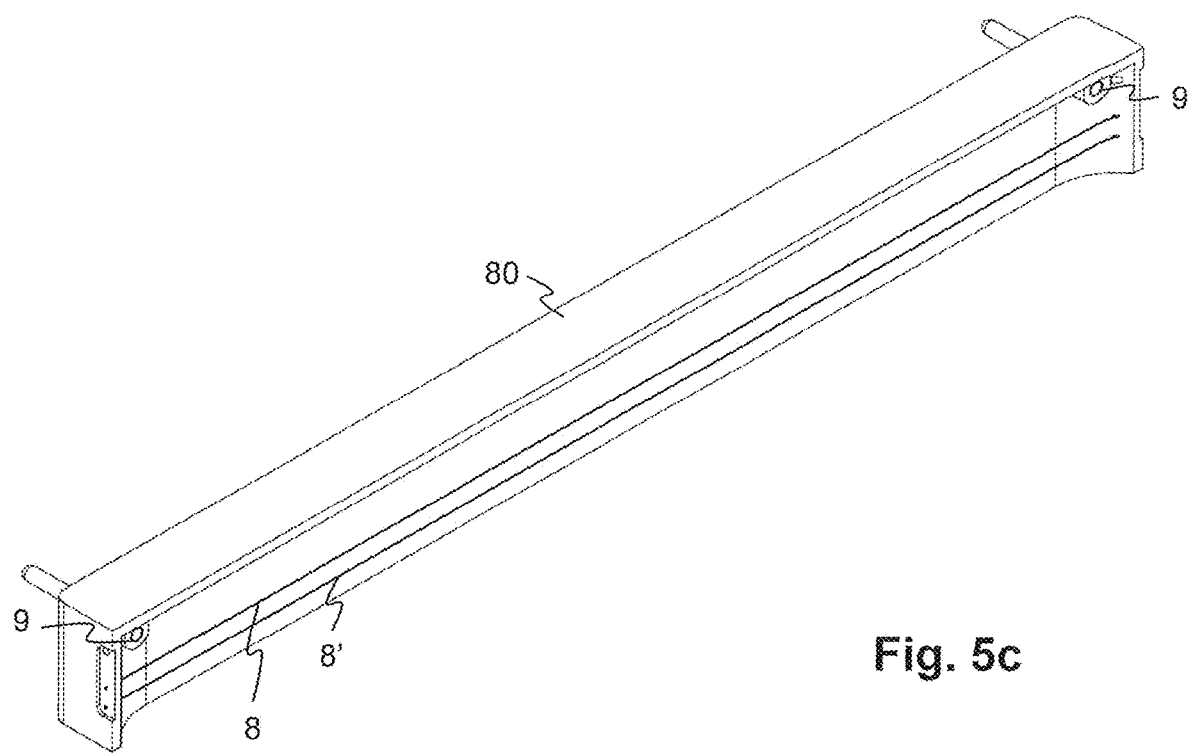

FIG. 5b shows an enlarged detail of the longitudinal side of the electrophoresis chamber of one of the two FIG. 4a or 4b, with a fastening means 9. The electrode wires 8 and 8' are led through a passage through a transverse wall, which lies transversely or perpendicularly to the longitudinal side and from there are led through a recess in the fastening means 9 and are fixed. The fastening means 9 leads from the inner side of the longitudinal side through an opening onto the outer side of the longitudinal side and there is connected to an electricity source.

Figure 6A:
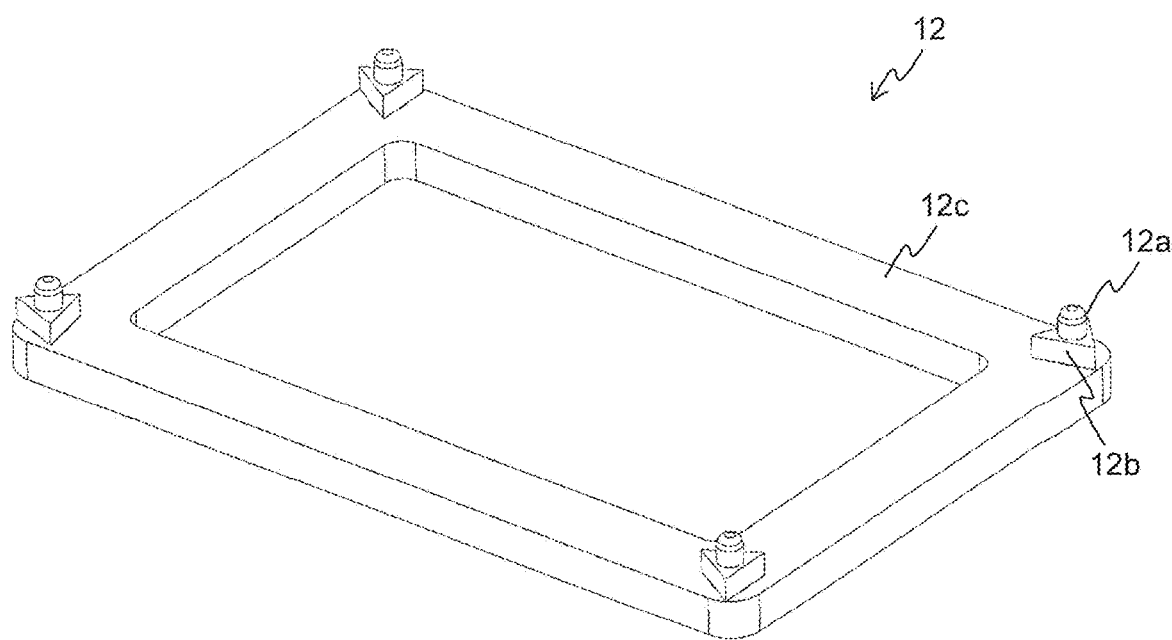
FIG. 6a shows a handling frame with pin-like prominences on triangular base parts, said prominences being at the corners.

FIG. 6a shows a handling frame 12, which at the corners includes triangular prominences 12b, thus a prominence with a triangular cross section, wherein the prominences 12b at the middle each include a pin-like extension 12a that latchably or positively fit into openings of the carrier plate, which are provided for these. After the latching, the carrier plate is fixedly connected to the handling frame 12.

Figure 6B:
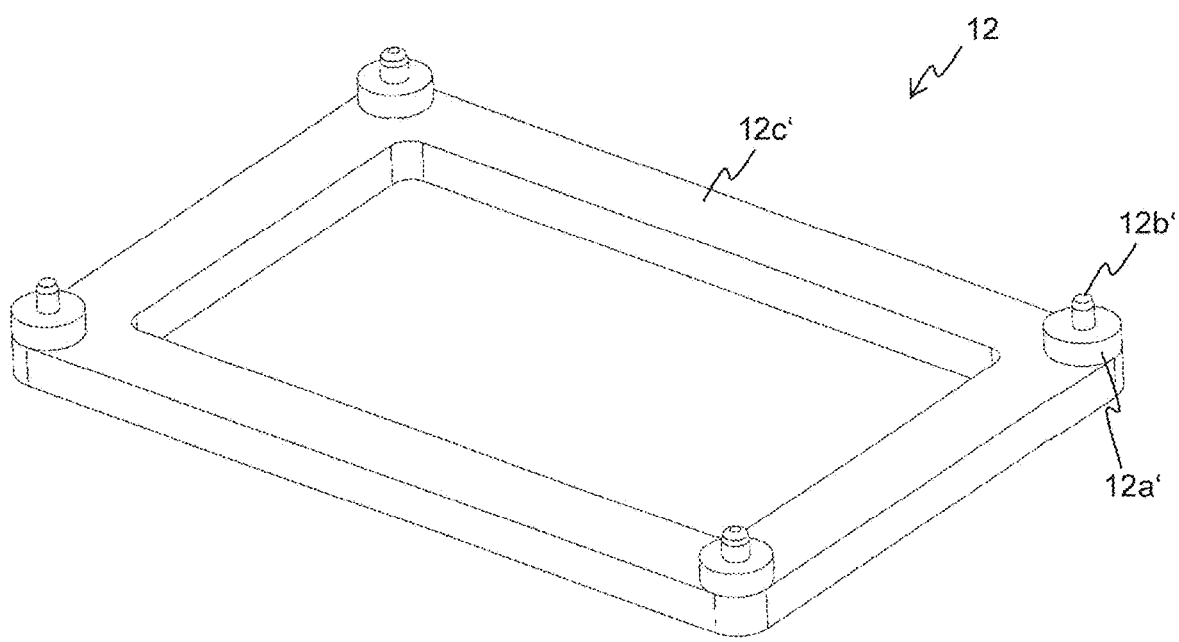
FIG. 6b shows a handling frame with pin-like prominences on round base parts, said prominences being at the corners.

FIG. 6b shows a further possible embodiment of a handling frame 12 with round prominences 12a' at the corners, each with pin-like extension 12b', which is central in this.

Figure 7A:
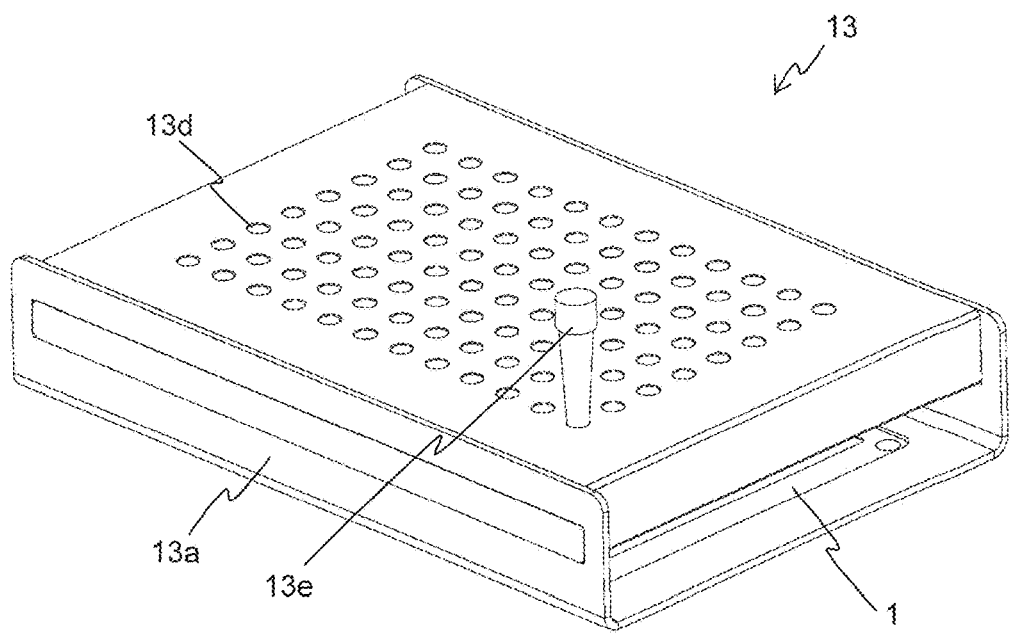
FIG. 7a shows a pipetting aid with a pipetting block and a frame and openings.

FIG. 7a shows a perspective view of a pipetting aid 13 with a pipetting block with 96 conical openings. The pipetting block in the region of a longitudinal side is not releasably, but rather is fixedly, connected to a frame 13a. In the region of transverse sides running transversely to the longitudinal side, the pipetting block is shorter than the frame that surrounds it, by 0.5 to 1 cm. In other words: the pipetting block with regard to one dimension is smaller than the frame.

Figure 7B:
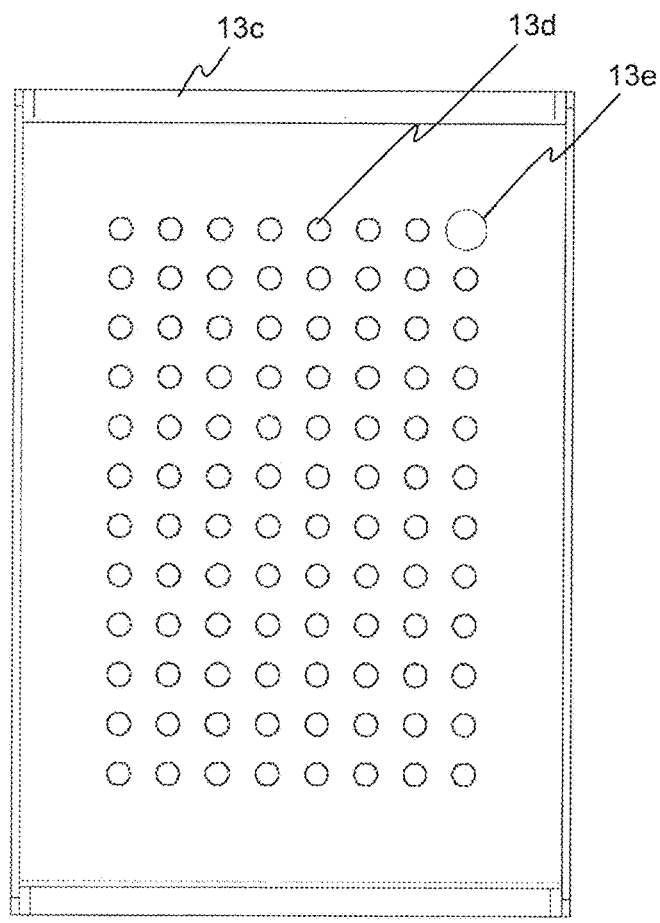
FIG. 7b shows a plan view of the pipetting aid with a pipette tip.
Figure 7C:
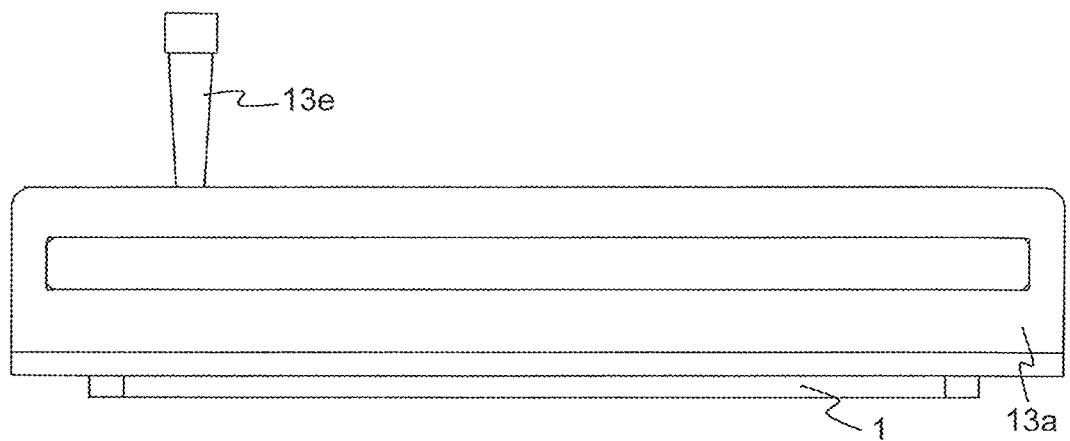
FIG. 7c shows a view of the longitudinal side of the pipetting aid with a metal frame and carrier plate.
Figure 7D:
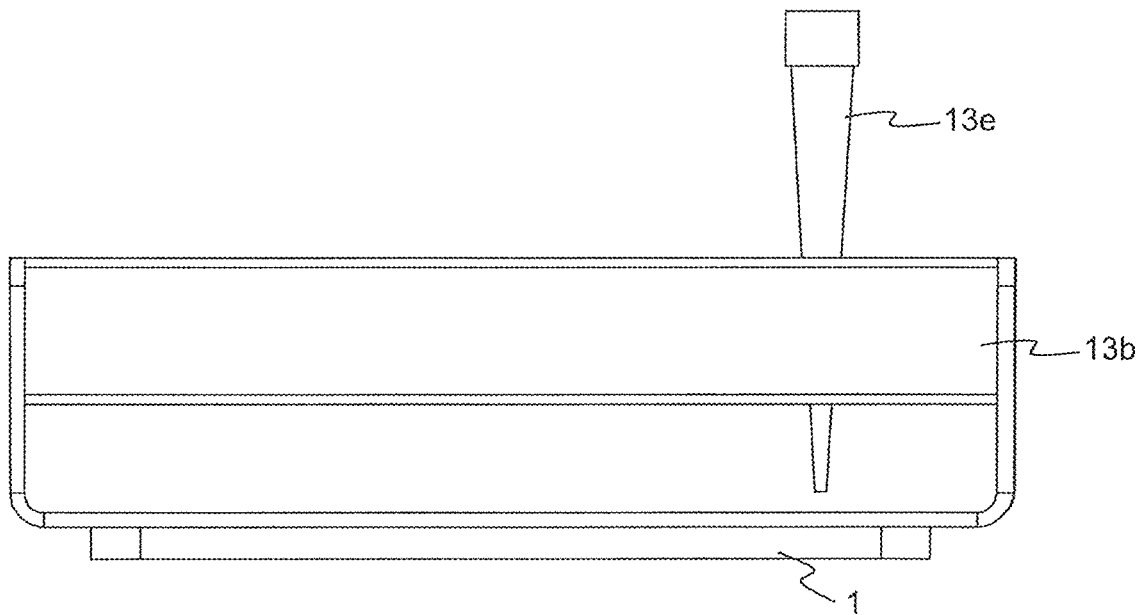
FIG. 7d shows a view of the transverse side of the pipetting aid with a pipetting block and carrier plate.

FIG. 7d shows a plan view of one of the transverse sides of the pipetting aid. The pipetting block 13b is not releasably connected to the frame. An intermediate space is located between the pipetting block 13b and the lower part of the frame.

FIG. 7b represents the upper side of the pipetting aid. The frame 13a is not designed in a continuous manner as is shown in FIG. 7a, but in the region of the lower side of the pipetting aid 13 includes a recess in the size of a carrier plate 1. The pipetting aid with the recess can be placed onto the carrier plate and fixed there in a slip-proof manner, for pipetting the gel spots onto the film.

FIG. 7c is a lateral view of the longitudinal side of the pipetting aid and shows the frame with a lateral recess, by which means the pipetting block is visible.

Figure 8A:
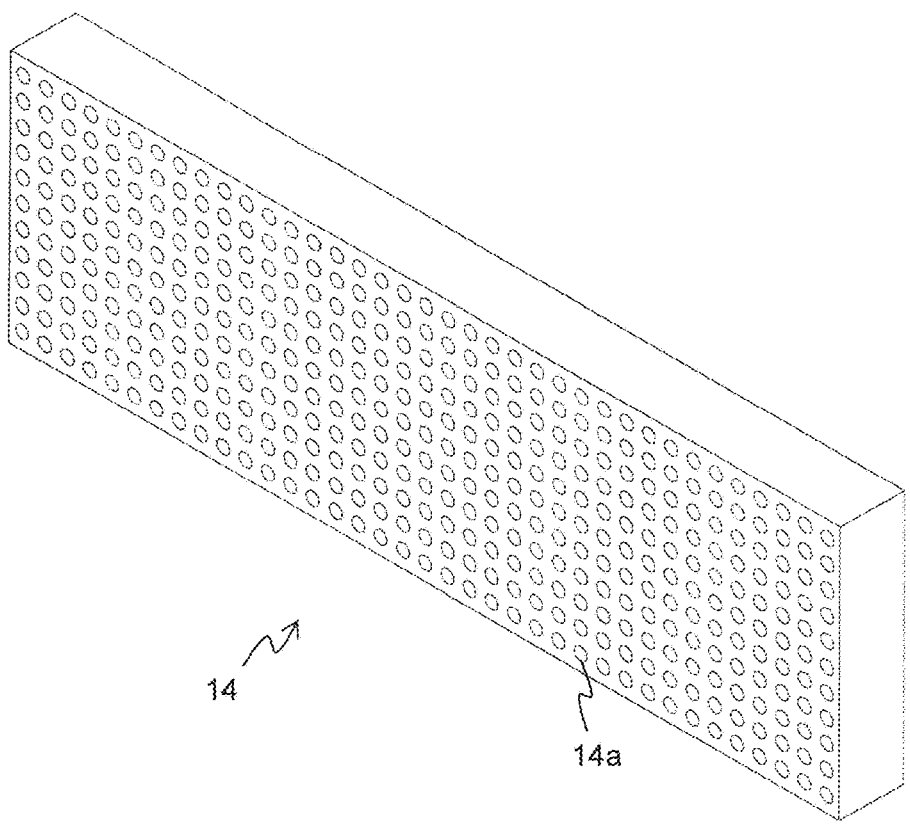
FIG. 8a shows a barrier with tubular passages.

FIG. 8a shows a barrier 14 with tubular passages 14a for the control of the buffer flow, the barrier being able to be attached, for example, in a side wall of an electrophoresis chamber. The buffer flow which is led out of a tube (not shown), for example, from a heating and/or cooling system is led through the tubular openings, broken up and thereby homogenised.

Figure 8B:
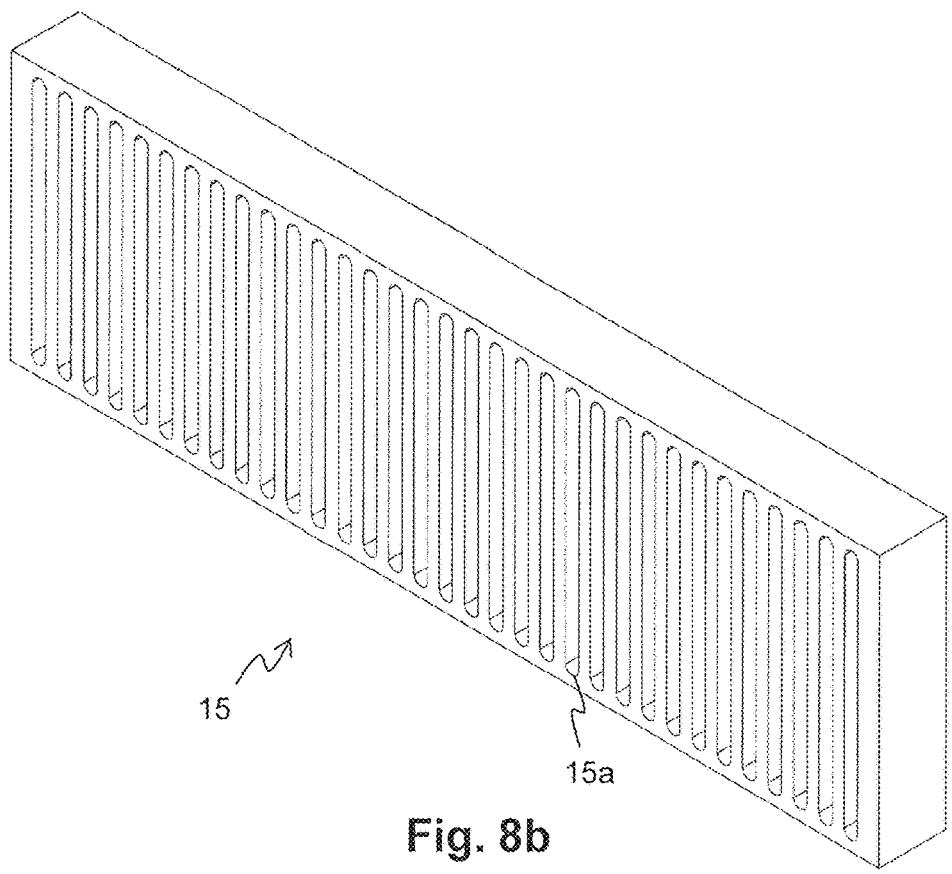
FIG. 8b shows a barrier with slot-like passages.

FIG. 8b shows an alternative barrier 15 for the control of the buffer flow, with slot-like passages 15a, which are aligned perpendicularly to the base of the electrophoresis chamber when the barrier is attached to a side wall of the electrophoresis chamber.

Figure 9A:
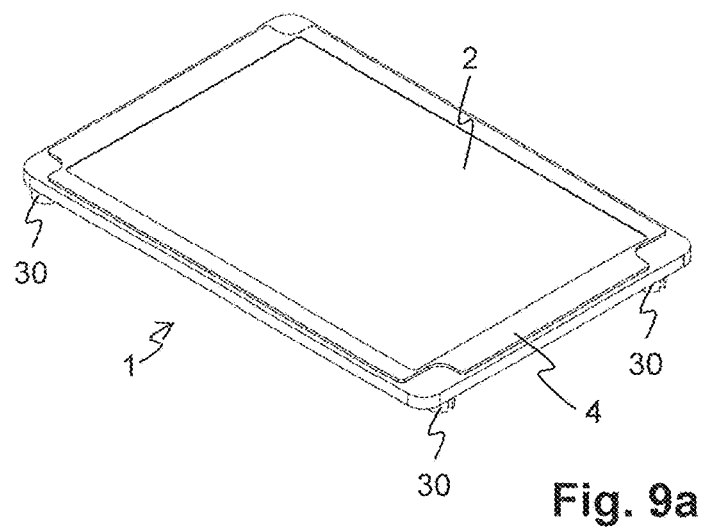
FIG. 9a, FIG. 9b, FIG. 9c are plan views of a carrier plate.
Figure 9B:
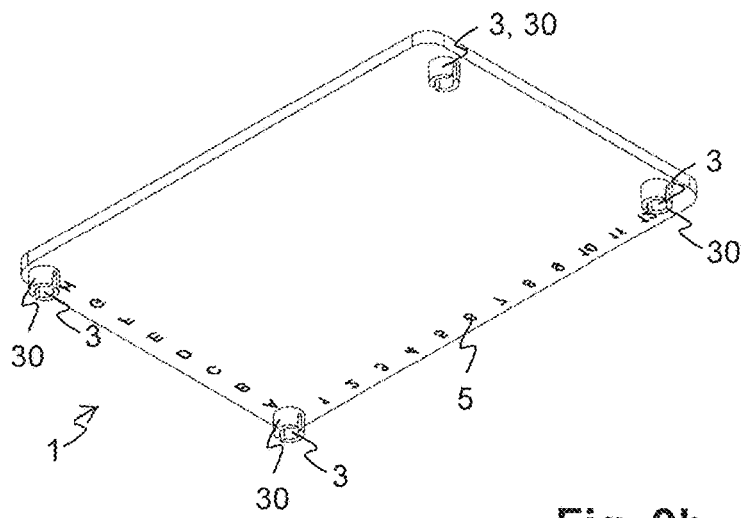

A plan view of the hydrophilic side of a carrier plate 1 is shown in FIG. 9a. FIG. 9b shows the side of the carrier plate 1 that is away from the hydrophilic side. A polyester film 2, which extends up to into the edge region 4 of the carrier plate 1, is arranged on the hydrophilic side of the carrier plate 1. The corner regions of the carrier plate 1 are free of polyester film 2. Four spacer elements 20, which each enclose an opening 3 in a hollow-cylinder-like manner, are arranged on the side of the carrier plate 1 that is opposite to the polyester film 2. Here, the two spacer elements 30 in the edge region 4 of the transverse side of the carrier plate 1 with markings 5 are spaced further from one another than the two spacer elements 30, which are arranged in the edge region 4 of the opposite transverse side of the carrier plate 1. The asymmetrical arrangement of the hollow-cylinder-like spacer elements 30 permits an orientation-specific positioning of the carrier plate 1 on the functional lid 7b and/or in the chamber 7a.

The hollow-cylinder-like spacer elements 30 include a slot that extends essentially along a longitudinal axis of the spacer element 30. The spacer element 30 obtains elastic or resilient characteristics by way of this slot, and these elastic characteristics permit a repeated, destruction-free positioning of the carrier plate 1 on the retaining element 6.

Figure 9C:
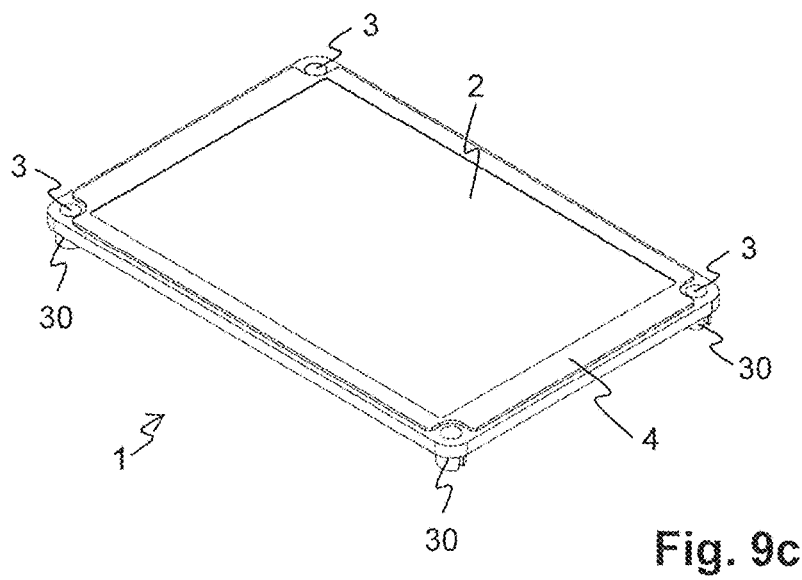

An alternative embodiment of a carrier plate 1, as is shown in FIG. 9a, is represented in FIG. 9c. Here, the carrier plate 1 includes continuous openings 3, which, similarly to FIGS. 9a and 9b, are surrounded by a hollow-cylinder-shaped spacer element 30. In contrast to this, the openings 3 of the carrier plate 1 in FIGS. 9a and 9b are not continuous, but are designed as blind holes. As is shown in FIG. 9c, the openings 3 and the spacer elements 30 can be arranged symmetrically in the corner region of the carrier plate 1.

Figure 10A:
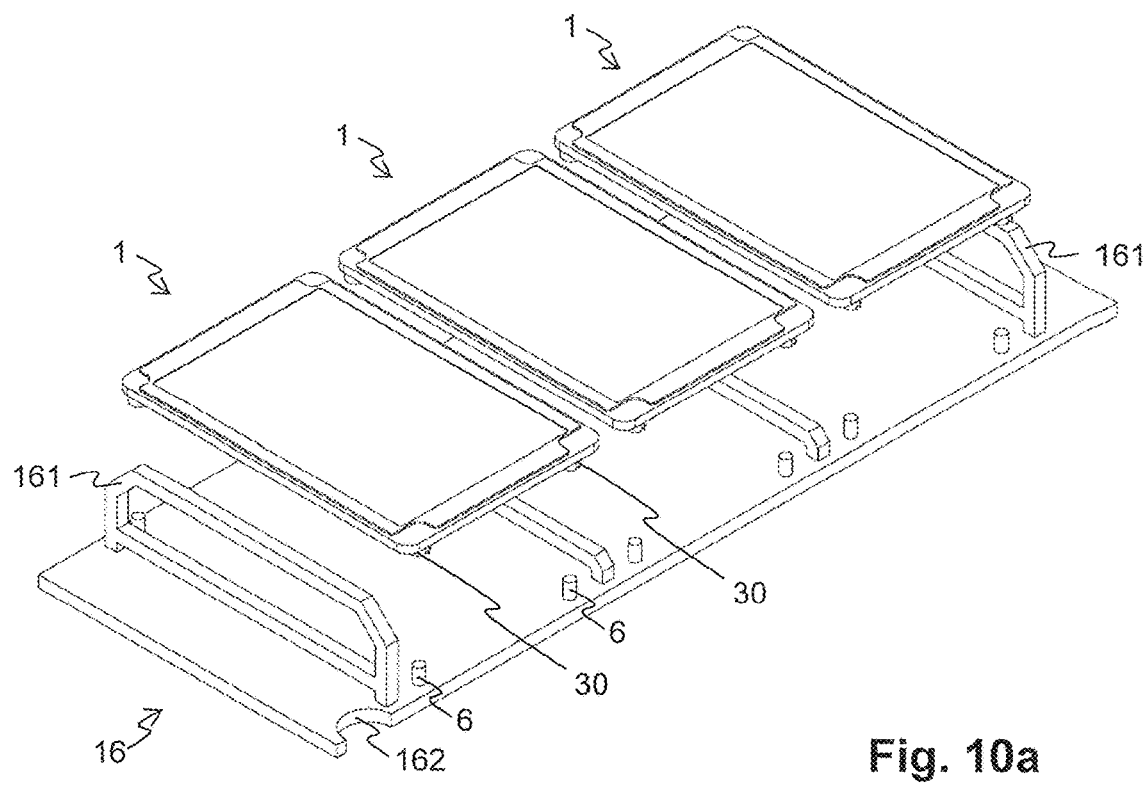
FIG. 10a and FIG. 10b show a carrier element with carrier plates.
Figure 10B:
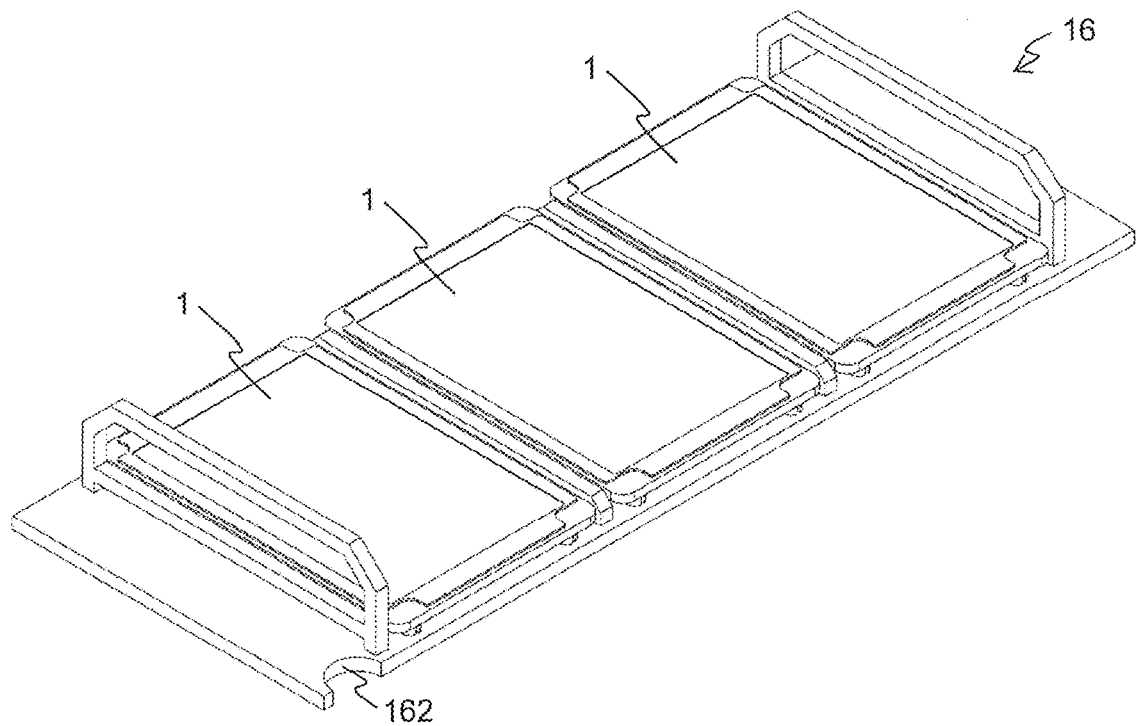

FIGS. 10a and 10b show a carrier element 16 with three carrier plates 1, as are shown in FIGS. 9a and 9b. The carrier element 16 includes twelve retaining elements 6. which are designed in a manner such that they receive and position the three carrier plates 1, thus fix them relative to the carrier element 16. FIG. 10b shows the carrier plate 1 in the positioned condition on the carrier element 16. The spacer elements 30 embrace the retaining elements 6 and the carrier plates 1 can be positioned in the homogenous, electrical field of the electrode pairs 8 in the chamber 7a with the help of the retaining elements 6. The polyester film 2, thus the hydrophilic side of the carrier plate 1 is arranged on the side that is away from the carrier element 16. The carrier element 16 includes an incorrect-rotation safeguard 162 that permits a specific, orientation-selective arrangement of the carrier element 16 in the chamber 7a. The carrier element 16 includes two carrier grips 161 that simplify the arranging of the carrier elements 16 in the chamber 7a of the electrophoresis tank 7.

Figure 10C:
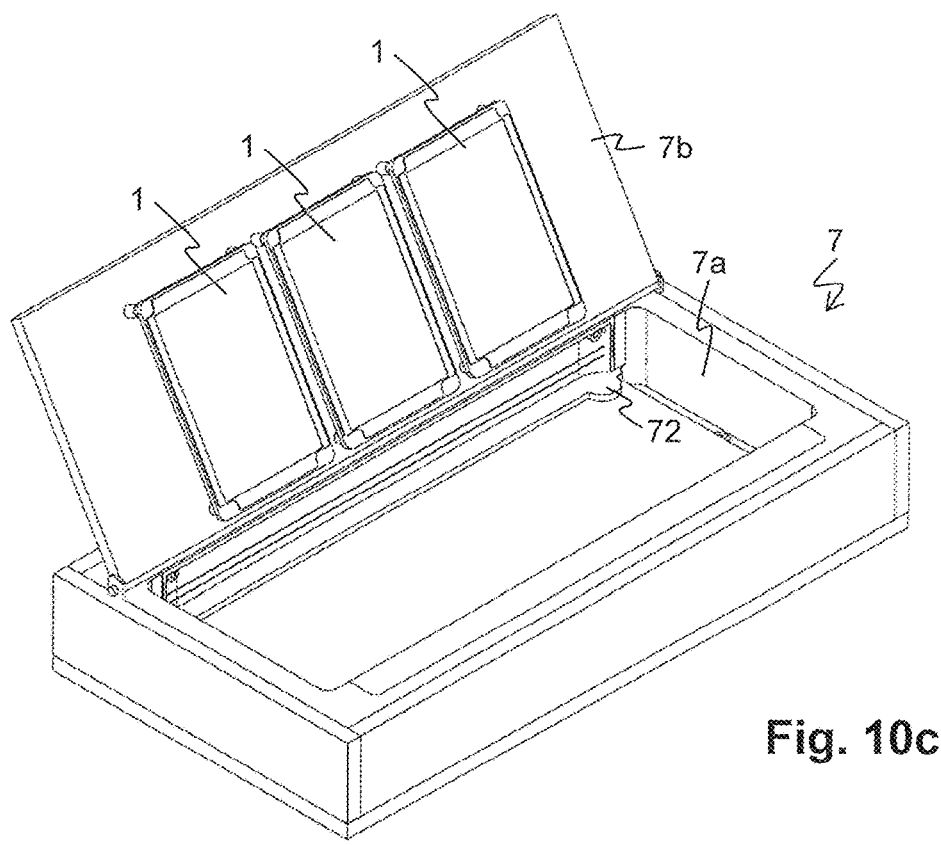
FIG. 10c is a plan view of an electrophoresis tank.

FIG. 10c shows a gel electrophoresis device in the opened condition, thus with an open functional lid 7b. Three carrier plates 1, which are fixed or positioned on respective retaining elements 6, are positioned on the functional lid 7b. An incorrect-rotation safeguard 72, which corresponds to the incorrect-rotation safeguard 162 of the carrier element 16, is arranged on the base of the chamber 7a.

Figure 10D:
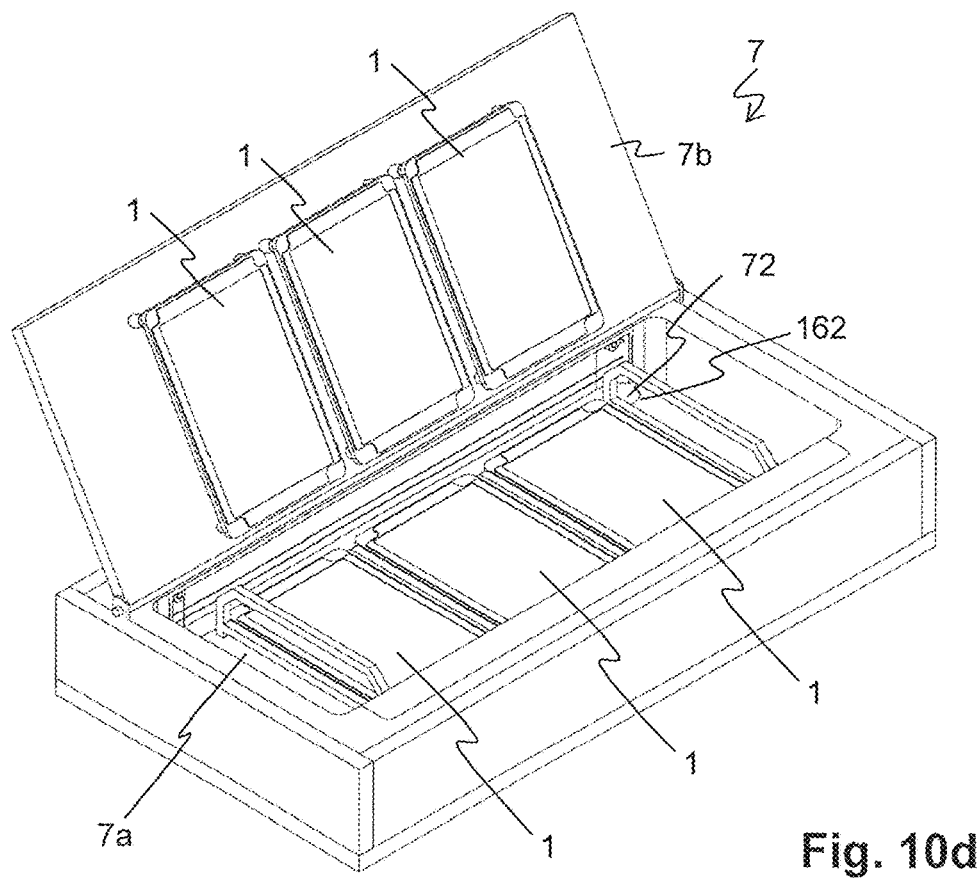
FIG. 10d is an electrophoresis tank with an inserted carrier element.

FIG. 10d shows the carrier element 16 with carrier plates 1 that are positioned thereon, the carrier element being inserted into the electrophoresis tank 7, in particular into the chamber 7a, as is shown in FIG. 10c. The incorrect-rotation safeguard 162 of the carrier element 16 engages into the incorrect-rotation safeguard on the base of the chamber 72 in an essentially exactly fitting manner. The specific, orientation-selective arrangement of the carrier element 16 in the chamber 7a is ensured by way of this. Six carrier plates 1 are therefore positioned on the electrophoresis tank 7 with the help of corresponding retaining elements 6.

Figure 11:
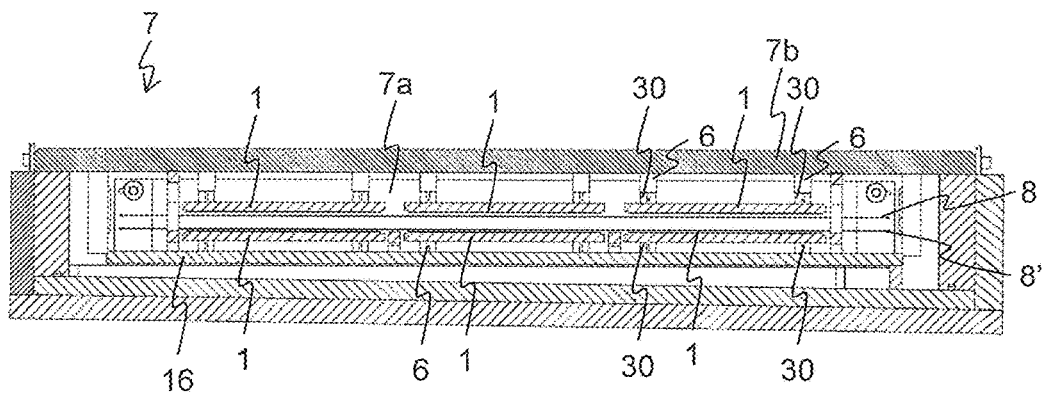
FIG. 11 show a cross section through the electrophoresis tank in the closed condition.

FIG. 11 shows the cross section through an electrophoresis tank in the closed condition, similarly as in FIG. 10d, but with a closed functional lid 7b. Three carrier plates 1 are fixed or positioned on the functional lid 7b with the help of retaining elements 6. Three further carrier plates 1 are fixed or positioned on the carrier element 16 with the help of retaining elements 6. The carrier element 16 is arranged on the base of the chamber 7a. The carrier element 16 is arranged in the chamber 7a in an orientation-specific manner with the help of the incorrect-rotation safeguard 162 on the base of the chamber 7a. The carrier plates 1 are positioned in the electrophoresis tank 7 in a face-to-face arrangement, wherein the electric field, which is produced by the electrode pairs 8, 8', is most homogeneous in the region of the hydrophilic surface of the carrier plate 1. As is shown in FIG. 11, the carrier plates 1 are arranged essentially at the height of the electrode pairs 8, 8' when the carrier element 16 with the positioned carrier plates 1 is inserted into the chamber 7a, and the function lid 7b with the positioned carrier plates 1 is closed.

The base of the chamber 7a has a slight descent, as is to be seen in FIG. 11. The gel electrophoresis buffer can be drained out of the chamber 7a in a simpler manner by way of this, which is to say that it can be exchanged essentially without any residue.

Figure 12A:
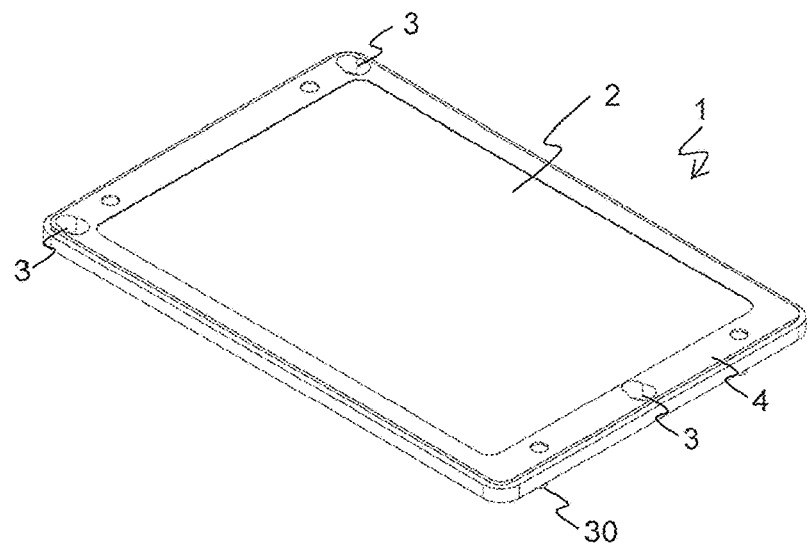
FIG. 12a and FIG. 12b show a carrier plate with openings and spacer elements.
Figure 12B:
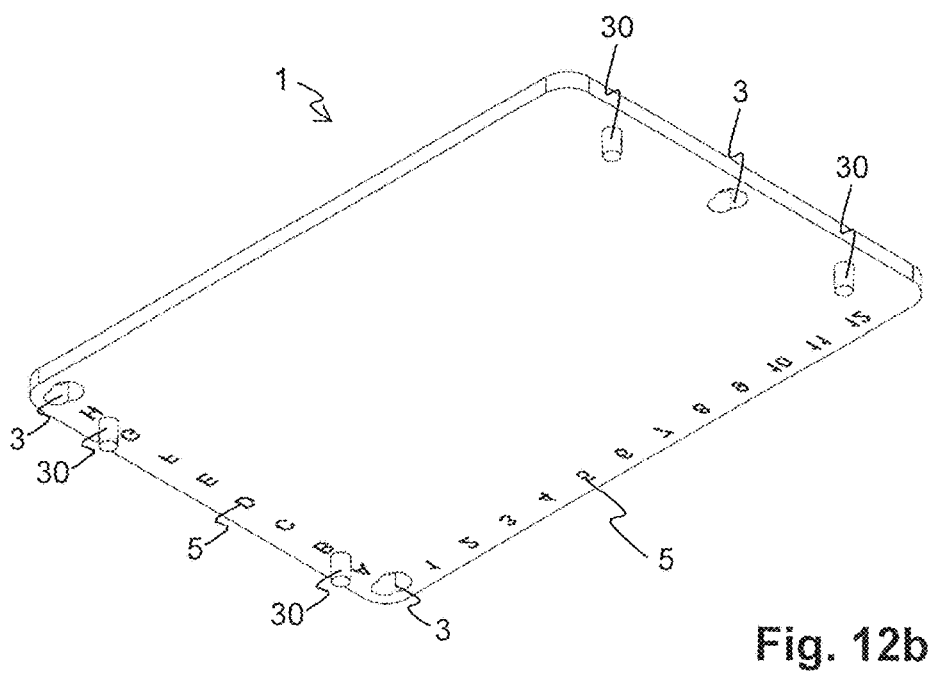

FIGS. 12a and 12b show a view of a carrier plate 1 with openings 3 and spacer elements 30. Similarly as in FIG. 9, the openings 3 and the spacer element 30 are arranged in the edge region 4 of the carrier plate 1. The openings 3 have a keyhole-shaped cross section with a first region and a second region. The first region has a larger diameter than the second region, wherein the first region is adjacent to the second region. In other words: the first region is essentially circular and the second region is designed as an indentation that connects to the first region. Four spacer elements 30 are arranged in the edge region 4 of the opposite transverse sides, on the side of the carrier pate 1 which is away from the hydrophilic side (see FIG. 12b). The spacer elements 30 serve for the simple stacking of carrier plates 1 above one another, wherein the spacer elements 30 of a first carrier plate 1 can be placed in a space-saving manner in the edge region 4 of a second carrier plate 1 without damaging samples/gel spots which are deposited on the hydrophilic side.

Figure 12C:
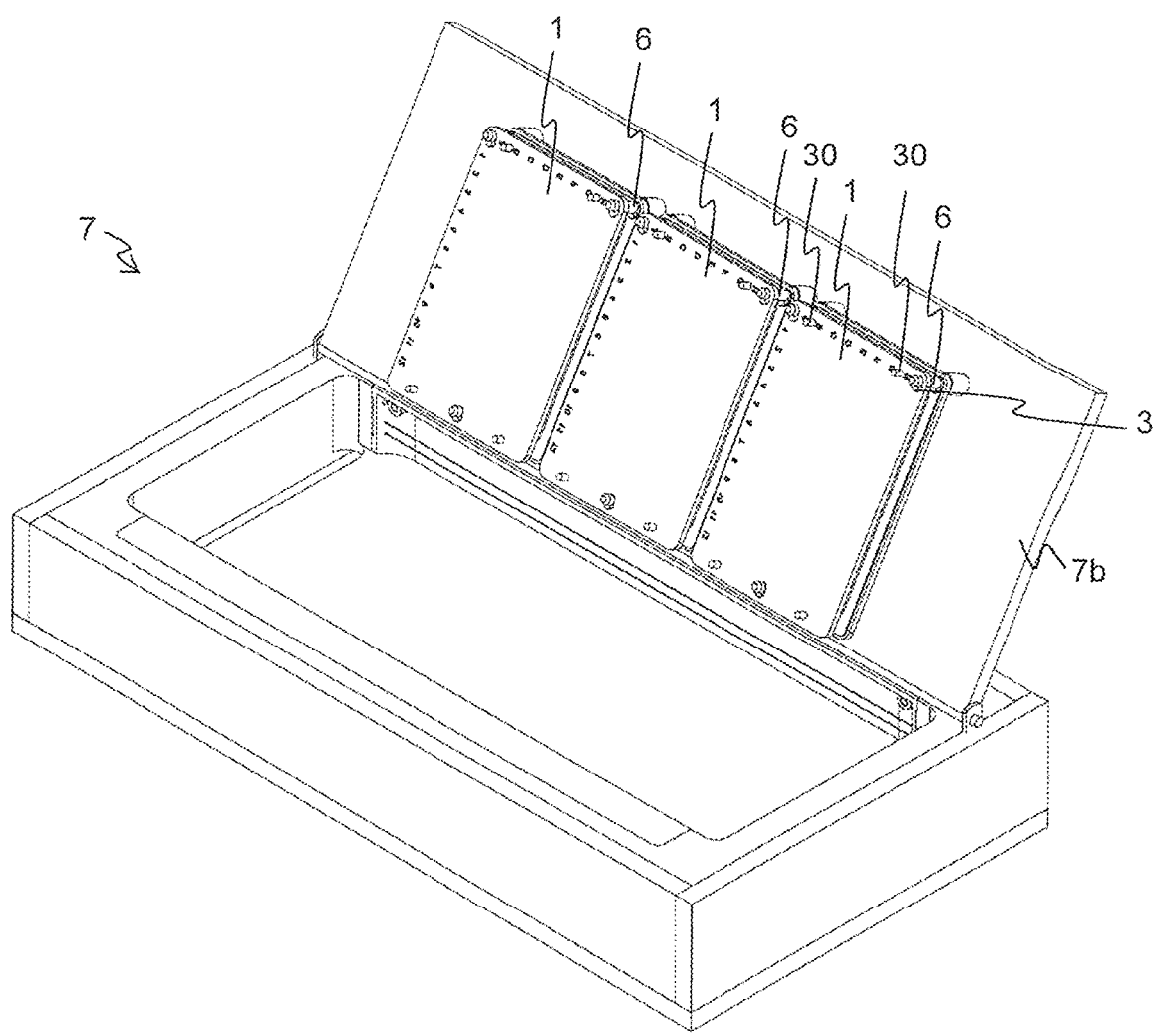
FIG. 12c shows an electrophoresis tank with carrier plates, which are positioned on the functional lid.

FIG. 12c shows an electrophoresis tank 7 with carrier plates 1, which are positioned on the functional lid 7b, as is shown in FIGS. 12a and 12b. The retaining element 6, which is fixed or fastened on the functional lid 7b, is designed in an essentially pin-like or mushroom-like manner and can engage into correspondingly congruent, which is to say correspondingly designed openings 3 of the carrier plate 1, wherein the latch-in section 6b of the retaining element 6 is positioned in the openings 3 of the carrier plate 1 in the positioned condition of the carrier plate 1.

The head part 6a is designed in a manner such that it fits through the first region of a keyhole-shaped opening 3 of the carrier plate 1. The head part can be pushed through this first region of the openings 3. The latch-in section 6b, which has a smaller diameter than the head part 6a, can subsequently be positioned or latched in, in the second region of the keyhole-shaped opening 3 of the carrier plate 1.

Figure 13:
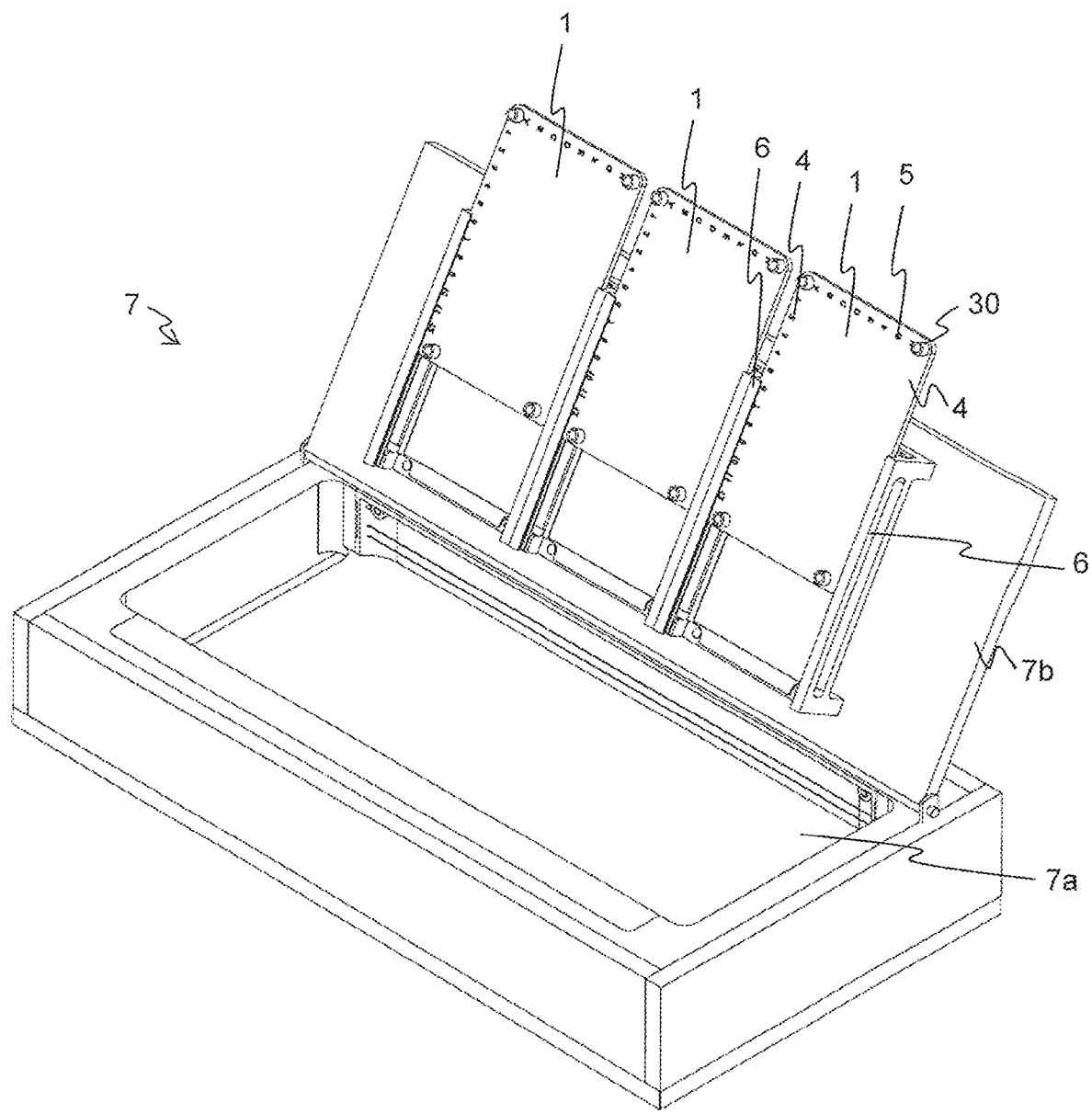
FIG. 13 an electrophoresis tank with rail-like retaining elements.

In FIG. 13, the retaining element 6 is designed in a rail-like manner with a groove as a latch-in section 6b, wherein the edge region 4 of the carrier plate 1 can be inserted or positioned in the groove of the retaining element. The head part 6a of the retaining element 6 is designed as a terminating surface.

The invention claimed is:

1. A gel electrophoresis device for single cell gel electrophoreses, said gel electrophoresis device comprises:
    a chamber for receiving a gel electrophoresis buffer,
    a lid for closing the chamber,
    at least one electrode pair for producing a homogeneous electrical field in the chamber, and
    at least one retaining element for receiving and positioning at least one carrier plate,
    wherein the at least one retaining element is configured to position the at least one carrier plate in the homogeneous electrical field which is produced by the at least one electrode pair,
    wherein the gel electrophoresis device comprises at least one measuring electrode for measuring an electrical field, said measuring electrode being different from the electrodes of the at least one electrode pair, and
    wherein the gel electrophoresis buffer can flow freely around the carrier plate.

2. The gel electrophoresis device according to claim 1, wherein the carrier plate comprises a planar surface.

3. The gel electrophoresis device according to claim 1, wherein at least one retaining element is arranged in the functional lid and/or on the base of the chamber.

4. The gel electrophoresis device according to claim 1, wherein the at least one retaining element is designed as the measuring electrode for measuring an electrical field.

5. The gel electrophoresis device according to claim 1, wherein the at least one retaining element comprises a head part and at least one latch-in section for the fixation of at least one carrier plate.

6. The gel electrophoresis device according to claim 5, wherein the at least one retaining element comprises a first latch-in section for the fixation of a first carrier plate and a second latch-in section for the fixation of a second carrier plate, a spacer between the first latch-in section and the second latch-in section and an anchor.

7. The gel electrophoresis device according to claim 1, wherein at least one barrier is arranged on a side of a wall of the chamber for producing a laminar buffer flow.

8. The gel electrophoresis device according to claim 7, wherein the at least one barrier comprises at least one continuous, horizontally running slot-like passage and/or several shorter slot-like, vertically running openings and/or tubular passages.

9. The gel electrophoresis device according to claim 1, wherein the gel electrophoresis device comprises a carrier element with at least one retaining element and the carrier element is positionable in the chamber.

10. The gel electrophoresis device according to claim 9, wherein the carrier element comprises an incorrect-rotation safeguard and wherein a corresponding incorrect-rotation safeguard is arranged on the base of the chamber.

11. A gel electrophoresis system for single cell electrophoreses with a high reproducibility, wherein the gel electrophoresis system comprises:
    a gel electrophoresis device according to claim 1 and
    in integrated means for the temperature control and/or
    an integrated means for cooling and/or heat generation and/or
    an integrated means for the buffer circulation and/or
    an integrated voltage generating device and/or
    an integrated mains connection device and/or
    integrative software and/or
    a subsequently arranged, integrated and automated analysis device for the quantification of the results and/or
    a digital interface for the further processing of the results.

12. A carrier plate for the positioning in a gel electrophoresis device according to claim 1, as well as for receiving at least one gel, wherein the carrier plate comprises a planar surface and
    a polyester film with a hydrophilic surface is deposited on said planar surface and/or
    the planar surface is treated with a hydrophilic layer.

13. The carrier plate according to claim 12, wherein the carrier plate comprises an edge region with at least one opening for receiving and positioning on at least one retaining element.

14. The carrier plate according to claim 13, wherein the carrier plate comprises an edge region with two openings and wherein at least one of the openings with regard to its shaping differs from the other openings.

15. The carrier plate according to claim 12, wherein the carrier plate comprises an alkali-resistant material with breakage strength of at least 15 to 20 Newton.

16. The carrier plate according to claim 12, wherein the carrier plate comprises a spacer element.

17. A handling frame for a carrier plate according to claim 12, wherein the handling frame comprises at least one fastening means for receiving the carrier plate, wherein the fastening means comprises a base part and a pin-like prominence.

18. A method for reproducibly carrying out a comet assay can whilst using the gel electrophoresis system according to claim 11, which comprises the following steps:

depositing the gel spot with the cells to be examined onto a carrier plate with the help of a single-channel or multi-channel pipette;
positioning the carrier plates on the at least one retaining element of the chamber;
closing a functional lid;
incubation of the carrier plates with the deposited gel spots in an alkaline environment for DNA unwinding;
selecting the electrophoresis program and initiating the control of the electrophoresis parameters by way of integrative software, for producing a homogeneous filed over the at least one carrier plate;
opening the functional lid and removing the carrier plate;
bringing the carrier plate into a staining solution;
drying gel spot in ethanol;
removing the carrier plate from the staining tank and bringing the carrier plate into a washing solution;
optional drying of the gel spot on the carrier plate;
manual or semi-automated or automated microscopic evaluation of the gel spot.

\* \* \* \* \*